(12) United States Patent
Hercouet

(10) Patent No.: US 7,582,121 B2
(45) Date of Patent: *Sep. 1, 2009

(54) COMPOSITION FOR DYEING KERATIN FIBERS, COMPRISING AT LEAST ONE DIAMINO-N,N-DIHYDROPYRAZOLONE DERIVATIVE, AT LEAST ONE COUPLER, AND AT LEAST ONE HETEROCYCLIC DIRECT DYE

(75) Inventor: Leïla Hercouet, Neuilly Plaisance (FR)

(73) Assignee: L'Oreal S.A., Paris (FR)

( * ) Notice: Subject to any disclaimer, the term of this patent is extended or adjusted under 35 U.S.C. 154(b) by 160 days.

This patent is subject to a terminal disclaimer.

(21) Appl. No.: 11/442,967

(22) Filed: May 31, 2006

(65) Prior Publication Data

US 2007/0006398 A1    Jan. 11, 2007

Related U.S. Application Data

(60) Provisional application No. 60/690,148, filed on Jun. 14, 2005.

(30) Foreign Application Priority Data

May 31, 2005   (FR) .................................. 05 51446

(51) Int. Cl.
  *A61Q 5/10*   (2006.01)
  *A01N 43/56*  (2006.01)
  *C07D 231/44* (2006.01)

(52) U.S. Cl. ....................... 8/405; 8/406; 8/407; 8/408; 8/410; 8/411; 8/412; 8/421; 8/567; 514/406; 514/407; 548/369.1

(58) Field of Classification Search ............... 8/405, 8/406, 407, 408, 410, 411, 412, 421, 567; 514/406, 407; 548/369.1

See application file for complete search history.

(56) References Cited

U.S. PATENT DOCUMENTS

| | | | |
|---|---|---|---|
| 3,649,158 A | 3/1972 | Kalopissis | |
| 4,003,699 A | 1/1977 | Rose et al. | |
| 4,128,425 A | 12/1978 | Greenwald | |
| RE30,199 E | 1/1980 | Rose et al. | |
| 4,314,808 A | 2/1982 | Jacquet et al. | |
| 4,823,985 A | 4/1989 | Grollier et al. | |
| 5,061,289 A | 10/1991 | Clausen et al. | |
| 5,089,025 A | 2/1992 | Rose et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Möckli | |
| 5,752,984 A | 5/1998 | Knuebel et al. | |
| 5,766,576 A | 6/1998 | Löwe et al. | |
| 5,865,855 A | 2/1999 | Doehling et al. | |
| 5,931,973 A | 8/1999 | Malle et al. | |
| 6,022,379 A | 2/2000 | Genard et al. | |
| 6,099,592 A | 8/2000 | Vidal et al. | |
| 6,099,593 A | 8/2000 | Terranova et al. | |
| 6,284,003 B1 | 9/2001 | Rose et al. | |
| 6,338,741 B1 | 1/2002 | Vidal et al. | |
| 6,391,064 B1 | 5/2002 | Baudry et al. | |
| 6,407,260 B1 | 6/2002 | Bonaventure et al. | |
| 6,432,146 B1 | 8/2002 | Rondeau | |
| 6,464,731 B1 | 10/2002 | Genet et al. | |
| 6,645,258 B2 | 11/2003 | Vidal et al. | |
| 6,692,538 B2 | 2/2004 | Bonaventure et al. | |
| 6,712,861 B2 | 3/2004 | Rondeau | |
| 6,730,789 B1 | 5/2004 | Birault et al. | |
| 6,773,463 B2 | 8/2004 | Pasquier et al. | |
| 6,884,265 B2 | 4/2005 | Vidal et al. | |
| 6,893,471 B2 | 5/2005 | Vidal | |
| 7,001,436 B2 | 2/2006 | Vidal et al. | |
| 7,285,137 B2 * | 10/2007 | Vidal et al. ..................... | 8/405 |
| 2001/0023514 A1 | 9/2001 | Cottard et al. | |
| 2003/0124079 A1 | 7/2003 | Mougin et al. | |
| 2003/0159222 A1* | 8/2003 | Javet et al. ..................... | 8/406 |
| 2003/0172475 A1 | 9/2003 | Desenne et al. | |
| 2004/0060126 A1 | 4/2004 | Cottard et al. | |
| 2004/0141943 A1 | 7/2004 | Mougin et al. | |
| 2004/0194228 A1 | 10/2004 | Lagrange | |

(Continued)

FOREIGN PATENT DOCUMENTS

DE   16 17 893   6/1971

(Continued)

OTHER PUBLICATIONS

STIC Search Report dated Jan. 18, 2008.*

(Continued)

*Primary Examiner*—Eisa B Elhilo
(74) *Attorney, Agent, or Firm*—Finnegan, Henderson, Farabow, Garrett & Dunner, LLP

(57) ABSTRACT

Disclose herein is a composition for dyeing keratin fibers, for example, human keratin fibers such as the hair, comprising at least one oxidation base chosen from diamino-N,N-dihydropyrazolones and addition salts thereof, at least one coupler, and at least one heterocyclic direct dye. Also disclosed herein is a method for dyeing keratin fibers comprising applying a composition of the present disclosure to the keratin fibers. The compositions and methods of the present disclosure may make it possible to obtain fast coloration of keratin fibers that is resistant to light and/or to washing.

36 Claims, No Drawings

U.S. PATENT DOCUMENTS

| | | | |
|---|---|---|---|
| 2004/0194229 | A1 | 10/2004 | Lagrange |
| 2004/0200009 | A1 | 10/2004 | Vidal |
| 2005/0000037 | A1 | 1/2005 | Audousset |
| 2005/0008594 | A1 | 1/2005 | Plos et al. |
| 2005/0039268 | A1 | 2/2005 | Plos et al. |
| 2005/0060815 | A1 | 3/2005 | Kravtchenko et al. |
| 2005/0076458 | A1 | 4/2005 | Cottard et al. |
| 2005/0166335 | A1 | 8/2005 | Vidal et al. |
| 2005/0183211 | A1 | 8/2005 | Samain et al. |
| 2005/0204483 | A1 | 9/2005 | Samain et al. |
| 2006/0070191 | A1 | 4/2006 | Lang et al. |

FOREIGN PATENT DOCUMENTS

| | | |
|---|---|---|
| DE | 23 59 399 | 6/1975 |
| DE | 38 25 212 | 2/1990 |
| DE | 38 43 892 | 6/1990 |
| DE | 41 33 957 | 4/1993 |
| DE | 42 34 885 | 4/1994 |
| DE | 44 04 564 | 8/1995 |
| DE | 195 43 988 | 5/1997 |
| DE | 197 30 412 | 12/1998 |
| DE | 101 18 271 | 3/2002 |
| DE | 201 04 441 | 7/2002 |
| DE | 101 48 847 | 4/2003 |
| EP | 0 173 109 | 3/1986 |
| EP | 0 714 954 | 6/1996 |
| EP | 0 770 375 | 5/1997 |
| EP | 0 984 010 | 3/2000 |
| EP | 1 025 834 | 8/2000 |
| EP | 1 166 753 | 1/2002 |
| EP | 1 166 754 | 1/2002 |
| EP | 1 170 000 | 1/2002 |
| EP | 1 170 001 | 1/2002 |
| EP | 1 197 203 | 4/2002 |
| EP | 1 437 123 | 7/2004 |
| EP | 1 464 327 | 10/2004 |
| EP | 1 473 023 | 11/2004 |
| EP | 1 550 656 | 7/2005 |
| EP | 1 598 047 | 11/2005 |
| FR | 1 584 111 | 12/1969 |
| FR | 2 456 764 | 12/1980 |
| FR | 2 586 913 | 3/1987 |
| FR | 2 733 749 | 11/1996 |
| FR | 2 746 392 | 9/1997 |
| FR | 2 750 048 | 12/1997 |
| FR | 2 760 010 | 8/1998 |
| FR | 2 782 452 | 2/2000 |
| FR | 2 788 273 | 7/2000 |
| FR | 2 798 931 | 3/2001 |
| FR | 2 801 308 | 5/2001 |
| FR | 2 803 195 | 7/2001 |
| FR | 2 811 993 | 1/2002 |
| FR | 2 817 467 | 6/2002 |
| FR | 2 822 696 | 10/2002 |
| FR | 2 825 622 | 12/2002 |
| FR | 2 825 625 | 12/2002 |
| FR | 2 825 702 | 12/2002 |
| FR | 2 825 703 | 12/2002 |
| FR | 2 833 834 | 6/2003 |
| FR | 2 845 387 | 4/2004 |
| FR | 2 848 837 | 6/2004 |
| FR | 2 848 840 | 6/2004 |
| FR | 2 855 966 | 12/2004 |
| FR | 2 855 967 | 12/2004 |
| GB | 1 026 978 | 4/1966 |
| GB | 1 153 196 | 5/1969 |
| GB | 1 213 697 | 11/1970 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 02/22093 | 3/2002 |

OTHER PUBLICATIONS

English Language Derwent Abstract for DE 101 18 271 (2002).
English Language Derwent Abstract for DE 101 48 847 (2003).
English Language Derwent Abstract for DE 201 04 441 (2002).
English Language Derwent Abstract for EP 0 770 375 (1997).
English Language Derwent Abstract for EP 1 197 203 (2002).
English Language Derwent Abstract for FR 2 456 764 (1980).
English Language Derwent Abstract for JP 2-19576 (1990).
English Language Derwent Abstract for JP 5-163124 (1993).
Co-pending U.S. Appl. No. 11/443,273, Composition for Dyeing Keratin Fibers, Comprising a Diamino-N,N-Dihydropyrazolone Derivative, A Coupler and a Polyol, Jean-Baptiste Saunier, filed May 31, 2006.
Co-pending U.S. Appl. No. 11/443,274, Composition for Dyeing Keratin Fibers, Comprising at Least one Diamino-N,N-Dihydropyrazolone Derivative, at Least one Coupler, and at Least one Surfactant, Jean-Baptiste Saunier, filed May 31, 2006.
Co-pending U.S. Appl. No. 11/443,353, Composition for Dyeing Keratin Fibers, Comprising at Least one Diamino-N,N-Dihydropyrazolone Derivative, at Least one Coupler and at Least one Associative Polyurethane Polymer, Jean-Baptiste Saunier, filed May 31, 2006.
European Search Report for EP 06 11 4654, mailed Aug. 23, 2006 (corresponding to U.S. Appl. No. 11/443,273).
European Search Report for EP 06 11 4652, mailed Aug. 23, 2006 (corresponding to U.S. Appl. No. 11/443,274).
European Search Report for EP 06 11 4656, mailed Sep. 22, 2006 (corresponding to U.S. Appl. No. 11/443,353).
European Search Report for EP 06 11 4655, mailed Sep. 22, 2006 (corresponding to the present application).
French Report for FR 05 51445, mailed Feb. 6, 2006 (corresponding to U.S. Appl. No. 11/443,273).
French Report for FR 05 51444, mailed Feb. 6, 2006 (corresponding to U.S. Appl. No. 11/443,274).
French Report for FR 05 51429, mailed Feb. 1, 2006 (corresponding to U.S. Appl. No. 11/443,353).
French Report for FR 05 51446, mailed Feb. 1, 2006 (corresponding to the present application).
Boros et al., *J. Het. Chem.*, 38(3): 613-616 (2001).
Cohen & Zand, *J. Am. Chem. Soc.*, 84: 586-590 (1962).
Fonnum et al., *Colloid Polym. Sci*, 271(4): 380-389 (1993).
Heyman & Snyder, *Tetrahedron. Letters*, 30: 2859-2862 (1973).
Kharasch & Bruice, *J. Am. Chem. Soc.*, 73: 3240-3244 (1951).
Lingens and Shneider-Bernlöhr, *Justus Liebig Ann. Chem.*, 686: 134-144 (1965).
Magnien & Baltzly, *J. Org. Chem.*, 23: 2029-2032 (1958).
Stenzl et al., *Helvetica Chimica Acta*, 33: 1183-1194 (1950).

\* cited by examiner

COMPOSITION FOR DYEING KERATIN FIBERS, COMPRISING AT LEAST ONE DIAMINO-N,N-DIHYDROPYRAZOLONE DERIVATIVE, AT LEAST ONE COUPLER, AND AT LEAST ONE HETEROCYCLIC DIRECT DYE

This application claims benefit of U.S. Provisional Application No. 60/690,148, filed Jun. 14, 2005, the contents of which are incorporated herein by reference. This application also claims benefit of priority under 35 U.S.C. § 119 to French Patent Application No. FR 05 51446, filed May 31, 2005, the contents of which are also incorporated herein by reference.

Disclosed herein is a composition for dyeing keratin fibers, for example, human keratin fibers such as the hair, comprising at least one oxidation base chosen from diamino-N,N-dihydropyrazolones and the addition salts thereof, at least one coupler, and at least one heterocyclic direct dye. Also disclosed herein is a method for dyeing keratin fibers comprising applying such a composition to the keratin fibers.

It is common practice to dye keratin fibers, for example, human keratin fibers such as the hair, with dye compositions comprising at least one oxidation dye precursor, such as ortho- or para-phenylenediamines, ortho- or para-aminophenols, and heterocyclic compounds such as diaminopyrazole derivatives, pyrazolo[1,5-a]pyrimidine derivatives, pyrimidine derivatives, pyridine derivatives, indole derivatives, and indoline derivatives, which are generally known as oxidation bases. Oxidation dye precursors, or oxidation bases, are colorless or weakly colored compounds that, when combined with oxidizing products, can give rise to colored compounds and dyes via a process of oxidative condensation. Permanent colorations may be thus obtained.

It is also known that the shades obtained with these oxidation bases may be varied by combining them with couplers and/or coloration modifiers, the latter being chosen, for example, from meta-phenylenediamines, meta-aminophenols, meta-hydroxyphenols, and heterocyclic compounds.

The variety of molecules available for use as oxidation bases and couplers allows a wide range of colors to be obtained.

The use of oxidation bases such as para-phenylenediamine and para-aminophenol derivatives may allow a broad range of colors to be obtained at basic pH, but may not always result in shades with good chromaticity, while at the same time giving the hair excellent properties, such as strength of color, variety of shades, uniformity of the color, and fastness with respect to external agents.

The use of these bases at neutral pH does not allow a varied range of shades to be produced, for example, warm shades such as reds and oranges.

Thus, the present disclosure provides novel compositions for dyeing keratin fibers that can make it possible to obtain a strong, chromatic, aesthetic, and/or sparingly selective coloration in varied shades, for example, natural shades, which may show good resistance to the various attacking factors to which the hair may be subjected, such as shampoo, light, sweat, and/or permanent reshaping operations.

Disclosed herein is a composition for dyeing keratin fibers, comprising, in a suitable medium:
(a) at least one oxidation base chosen from diamino-N,N-dihydropyrazolone compounds of formula (I) and addition salts thereof:

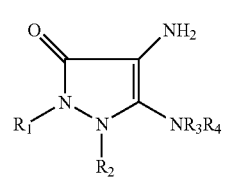

wherein:
$R_1$, $R_2$, $R_3$, and $R_4$, which may be identical or different, are chosen from:
linear and branched $C_1$-$C_{10}$, for example, $C_1$-$C_6$, alkyl radicals optionally substituted with at least one radical chosen from $OR_5$ radicals, $NR_6R_7$ radicals, carboxyl radicals, sulfonic radicals, carboxamido radicals $CONR_6R_7$, sulfonamido radicals $SO_2NR_6R_7$, and heteroaryl and aryl radicals optionally substituted with at least one group chosen from ($C_1$-$C_4$)alkyl, hydroxyl, $C_1$-$C_2$ alkoxy, amino, and (di)($C_1$-$C_2$)alkylamino groups;
aryl radicals optionally substituted with at least one raical chosen from ($C_1$-$C_4$)alkyl, hydroxyl, $C_1$-$C_2$ alkoxy, amino, and (di)($C_1$-$C_2$)alkylamino radicals;
5- or 6-membered heteroaryl radicals, optionally substituted with at least one radical chosen from ($C_1$-$C_4$) alkyl and ($C_1$-$C_2$)alkoxy radicals;
$R_3$ and $R_4$ may also be hydrogen;
$R_5$, $R_6$, and $R_7$, which may be identical or different, are chosen from:
hydrogen;
linear and branched $C_1$-$C_4$ alkyl radicals optionally substituted with at least one radical chosen from hydroxyl, $C_1$-$C_2$ alkoxy, carboxamido $CONR_8R_9$, sulfonyl $SO_2R_8$, and aryl radicals optionally substituted with at least one radical chosen from ($C_1$-$C_4$) alkyl, hydroxyl, $C_1$-$C_2$ alkoxy, amino, and (di)($C_1$-$C_2$)alkylamino radicals; and
aryl radicals optionally substituted with at least one radical chosen from ($C_1$-$C_4$)alkyl, hydroxyl, $C_1$-$C_2$ alkoxy, amino, and (di)($C_1$-$C_2$)alkylamino radicals;
$R_6$ and $R_7$, which may be identical or different, may also be chosen from carboxamido radicals $CONR_8R_9$ and sulfonyl radicals $SO_2R_8$;
$R_8$ and $R_9$, which may be identical or different, are chosen from hydrogen and linear and branched $C_1$-$C_4$ alkyl radicals optionally substituted with at least one radical chosen from hydroxyl and $C_1$-$C_2$ alkoxy radicals;
$R_1$ and $R_2$, and $R_3$ and $R_4$, may form, together with the nitrogen atoms to which they are attached, a saturated or unsaturated 5- to 7-membered heterocycle optionally substituted with at least one entity chosen from halogen atoms, amino radicals, (di)($C_1$-$C_4$)alkylamino radicals, hydroxyl radicals, carboxyl radicals, carboxamido radicals, ($C_1$-$C_2$)alkoxy radicals, and $C_1$-$C_4$ alkyl radicals optionally substituted with at least one radical chosen from hydroxyl, amino, (di)alkylamino, alkoxy, carboxyl, and sulfonyl radicals; and
$R_3$ and $R_4$ may also form, together with the nitrogen atom to which they are attached, a 5- or 7-membered heterocycle, the carbon atoms of which may be replaced with at least one entity chosen from oxygen and optionally substituted nitrogen;
(b) at least one coupler; and
(c) at least one heterocyclic direct dye.

The compositions and methods of the present disclosure can make it possible to obtain a strong, aesthetic, and/or sparingly selective coloration of keratin fibers in varied shades, which may show good resistance to the various attacking factors to which the hair may be subjected, such as shampoo, light, sweat, and/or permanent reshaping operations. The compositions and methods of the present disclosure can also make it possible to obtain natural shades. The compositions and methods of the present disclosure furthermore may make it possible to obtain intense and varied colorations at neutral pH.

Also disclosed herein is a method for dyeing keratin fibers comprising applying the composition of the present disclosure to the keratin fibers.

Further disclosed herein is a dyeing kit comprising at least one compartment comprising a dye composition comprising at least one oxidation base of formula (I), at least one coupler, and at least one heterocyclic direct dye, and, at least one separate compartment comprising an oxidizing composition comprising at least one oxidizing agent.

As used herein, the term "alkyl radical" means linear and branched alkyl radicals which are $C_1$-$C_{10}$ unless otherwise indicated, for example, $C_1$-$C_6$, or $C_1$-$C_4$, such as methyl, ethyl, propyl, isopropyl, isobutyl, tert-butyl, pentyl, and hexyl radicals.

As used herein, the term "hydroxyalkyl radical" means alkyl radicals which are mono- or polysubstituted with at least one hydroxyl radical, i.e., an alkyl radical that may be substituted with at least one hydroxyl radical.

As used herein, the expression "ranging from x to y" means in the range from x to y, the limits x and y being included.

Oxidation Bases

In at least one embodiment, in formula (I), the radicals $R_1$ and $R_2$, which may be identical or different, are chosen from:
$C_1$-$C_6$ alkyl radicals optionally substituted with at least one radical chosen from hydroxyl, ($C_1$-$C_2$)alkoxy, amino, and (di)($C_1$-$C_2$)alkylamino radicals; and
phenyl, methoxyphenyl, ethoxyphenyl, and benzyl radicals.

In another embodiment, the radicals $R_1$ and $R_2$, which may be identical or different, may be chosen from methyl, ethyl, 2-hydroxyethyl, 3-hydroxypropyl, 2-hydroxypropyl, and phenyl radicals.

According to still another embodiment, the radicals $R_1$ and $R_2$ may form, together with the nitrogen atoms to which they are attached, a saturated or unsaturated, optionally substituted 5- or 6-membered ring.

In yet another embodiment, the radicals $R_1$ and $R_2$ may form, together with the nitrogen atoms to which they are attached, a ring chosen from pyrazolidine and pyridazolidine rings, optionally substituted with at least one radical chosen from $C_1$-$C_4$ alkyl, hydroxyl, ($C_1$-$C_2$)alkoxy, carboxyl, carboxamido, amino, andr (di)($C_1$-$C_2$)alkylamino radicals.

In a further embodiment, the radicals $R_1$ and $R_2$ may form, together with the nitrogen atoms to which they are attached, a ring chosen from pyrazolidine and pyridazolidine rings.

The radicals $R_3$ and $R_4$, which may be identical or different, may, in at least one embodiment, be chosen from hydrogen; linear and branched $C_1$-$C_6$ alkyl radicals optionally substituted with at least one radical chosen from hydroxyl, ($C_1$-$C_2$) alkoxy, amino, and (di)($C_1$-$C_2$)alkylamino radicals; and phenyl radicals optionally substituted with at least one radical chosen from hydroxyl, amino, and ($C_1$-$C_2$)alkoxy radicals.

In one embodiment, the radicals $R_3$ and $R_4$, which may be identical or different, may be chosen from hydrogen, methyl radicals, ethyl radicals, isopropyl radicals, 2-hydroxyethyl radicals, 3-hydroxypropyl radicals, 2-hydroxypropyl radicals, and 2-carboxyethyl radicals. According to another embodiment, the radicals $R_3$ and $R_4$ may be hydrogen.

In yet another embodiment, the radicals $R_3$ and $R_4$ may form, together with the nitrogen atom to which they are attached, a 5- or 7-membered ring chosen from pyrrolidine, piperidine, homopiperidine, piperazine, and homopiperazine heterocycles; said rings possibly being substituted with at least one radical chosen from hydroxyl, amino, (di)($C_1$-$C_2$) alkylamino, carboxyl, carboxamido, and $C_1$-$C_4$ alkyl radicals optionally substituted with at least one radical chosen from hydroxyl, amino, and $C_1$-$C_2$ (di)alkylamino radicals.

According to a further embodiment, the radicals $R_3$ and $R_4$ may form, together with the nitrogen atom to which they are attached, a 5- or 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine, and N-(2-hydroxyethyl)homopiperazine.

In another embodiment, the radicals $R_3$ and $R_4$ may form, together with the nitrogen atom to which they are attached, a 5- or 7-membered ring chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, hydroxypiperidine, homopiperidine, diazepane, N-methylhomopiperazine, and N-β-hydroxyethylhomopiperazine.

In accordance with yet another embodiment of the present disclosure, the radicals $R_3$ and $R_4$ may form, together with the nitrogen atom to which they are attached, a 5-membered ring, such as pyrrolidine, 3-hydroxypyrrolidine, 3-aminopyrrolidine, and 3-dimethylaminopyrrolidine.

The compounds of formula (I) may be optionally salified with at least one acid chosen from strong mineral acids, for instance, HCl, HBr, HI, $H_2SO_4$, and $H_3PO_4$; and organic acids, for instance, acetic acid, lactic acid, tartaric acid, citric acid, succinic acid, benzenesulfonic acid, para-toluenesulfonic acid, formic acid, and methanesulfonic acid.

The compounds of formula (I) may also be in the form of solvates, for example, hydrates and solvates of linear or branched alcohols such as ethanol and isopropanol.

Examples of derivatives of formula (I) include, but are not limited to:
4,5-diamino-1,2-dimethyl-1,2-dihydropyrazol-3-one;
4-amino-5-methylamino-1,2-dimethyl-1,2-dihydropyrazol-3-one;
4-amino-5-dimethylamino-1,2-dimethyl-1,2-dihydropyrazol-3-one;
4-amino-5-(2-hydroxyethyl)amino-1,2-dimethyl-1,2-dihydropyrazol-3-one;
4-amino-5-(pyrrolidin-1-yl)-1,2-dimethyl-1,2-dihydropyrazol-3-one;
4-amino-5-(piperid-1-yl)-1,2-dimethyl-1,2-dihydropyrazol-3-one;

4,5-diamino-1,2-di(2-hydroxyethyl)-1,2-dihydropyrazol-3-one;
4-amino-5-methylamino-1,2-di(2-hydroxyethyl)-1,2-dihydropyrazol-3-one;
4-amino-5-dimethylamino-1,2-di(2-hydroxyethyl)-1,2-dihydropyrazol-3-one;
4-amino-5-(2-hydroxyethyl)amino-1,2-di(2-hydroxyethyl)-1,2-dihydropyrazol-3-one;
4-amino-5-(pyrrolidin-1-yl)-1,2-di(2-hydroxyethyl)-1,2-dihydropyrazol-3-one;
4-amino-5-(piperid-1-yl)-1,2-di(2-hydroxyethyl)-1,2-dihydropyrazol-3-one;
4,5-diamino-1,2-diethyl-1,2-dihydropyrazol-3-one;
4,5-diamino-1,2-phenyl-1,2-dihydropyrazol-3-one;
4,5-diamino-1-ethyl-2-methyl-1,2-dihydropyrazol-3-one;
4,5-diamino-2-ethyl-1-methyl-1,2-dihydropyrazol-3-one;
4,5-diamino-1-phenyl-2-methyl-1,2-dihydropyrazol-3-one;
4,5-diamino-2-phenyl-1-methyl-1,2-dihydropyrazol-3-one;
4,5-diamino-1-(2-hydroxyethyl)-2-methyl-1,2-dihydropyrazol-3-one;
4,5-diamino-2-(2-hydroxyethyl)-1-methyl-1,2-dihydropyrazol-3-one;
2,3-diamino-6,7-dihydro-1H,5H-pyrazolo[1,2-a]pyrazol-1-one;
2-amino-3-methylamino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(2-hydroxyethyl)amino-6,7-dihydro-1H,5H-pyrazolo[1,2-a]pyrazol-1-one;
2-amino-3-(2-hydroxypropyl)amino-6,7-dihydro-1H,5H-pyrazolo[1,2-a]pyrazol-1-one;
2-amino-3-bis(2-hydroxyethyl)amino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
2-amino-3-(3-hydroxypyrrolidin-1-yl)-6,7-dihydro-1H,5H-pyrazolo[1,2-a]pyrazol-1-one;
2-amino-3-(piperid-1-yl)-6,7-dihydro-1H,5H-pyrazolo[1,2-a]pyrazol-1-one;
2,3-diamino-6-hydroxy-6,7-dihydro-1H,5H-pyrazolo[1,2-a]pyrazol-1-one;
2,3-diamino-6-methyl-6,7-dihydro-1H,5H-pyrazolo[1,2-a]pyrazol-1-one;
2,3-diamino-6-dimethyl-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
2,3-diamino-5,8-dihydro-1H,6H-pyridazino[1,2-a]pyrazol-1-one;
4-amino-5-dimethylamino-1,2-diethyl-1,2-dihydropyrazol-3-one;
4-amino-1,2-diethyl-5-ethylamino-1,2-dihydropyrazol-3-one;
4-amino-1,2-diethyl-5-isopropylamino-1,2-dihydropyrazol-3-one;
4-amino-1,2-diethyl-5-(2-hydroxyethylamino)-1,2-dihydropyrazol-3-one;
4-amino-5-(2-dimethylaminoethylamino)-1,2-diethyl-1,2-dihydropyrazol-3-one;
4-amino-5-[bis(2-hydroxyethyl)amino]-1,2-diethyl-1,2-dihydropyrazol-3-one;
4-amino-1,2-diethyl-5-(3-imidazol-1-ylpropylamino)-1,2-dihydropyrazol-3-one;
4-amino-5-dimethylamino-1,2-diethyl-1,2-dihydropyrazol-3-one;
4-amino-1,2-diethyl-5-ethylamino-1,2-dihydropyrazol-3-one;
4-amino-1,2-diethyl-5-isopropylamino-1,2-dihydropyrazol-3-one;
4-amino-1,2-diethyl-5-(2-hydroxyethylamino)-1,2-dihydropyrazol-3-one;
4-amino-5-(2-dimethylaminoethylamino)-1,2-diethyl-1,2-dihydropyrazol-3-one;
4-amino-5-[bis(2-hydroxyethyl)amino]-1,2-diethyl-1,2-dihydropyrazol-3-one;
4-amino-1,2-diethyl-5-(3-imidazol-1-ylpropylamino)-1,2-dihydropyrazol-3-one;
4-amino-1,2-diethyl-5-(3-hydroxypyrrolidin-1-yl)-1,2-dihydropyrazol-3-one;
4-amino-1,2-diethyl-5-pyrrolidin-1-yl-1,2-dihydropyrazol-3-one;
4-amino-5-(3-dimethylaminopyrrolidin-1-yl)-1,2-diethyl-1,2-dihydropyrazol-3-one;
4-amino-1,2-diethyl-5-(4-methylpiperazin-1-yl)pyrazolidin-3-one;
2,3-diamino-6-hydroxy-6,7-dihydro-5H-pyrazolo[1,2-a]pyrazol-1-one; and
the addition salts thereof;

some of which are depicted below to illustrate the names with the corresponding chemical structures:

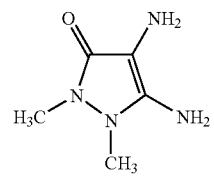
4,5-diamino-1,2-dimethyl-1,2-dihydropyrazol-3-one

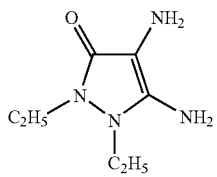
4,5-diamino-1,2-diethyl-1,2-dihydropyrazol-3-one

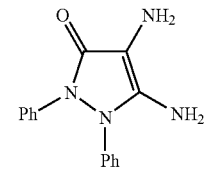
4,5-diamino-1,2-diphenyl-1,2-dihydropyrazol-3-one

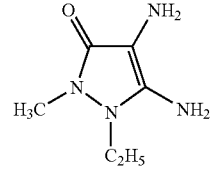
4,5-diamino-1-ethyl-2-methyl-1,2-dihydropyrazol-3-one

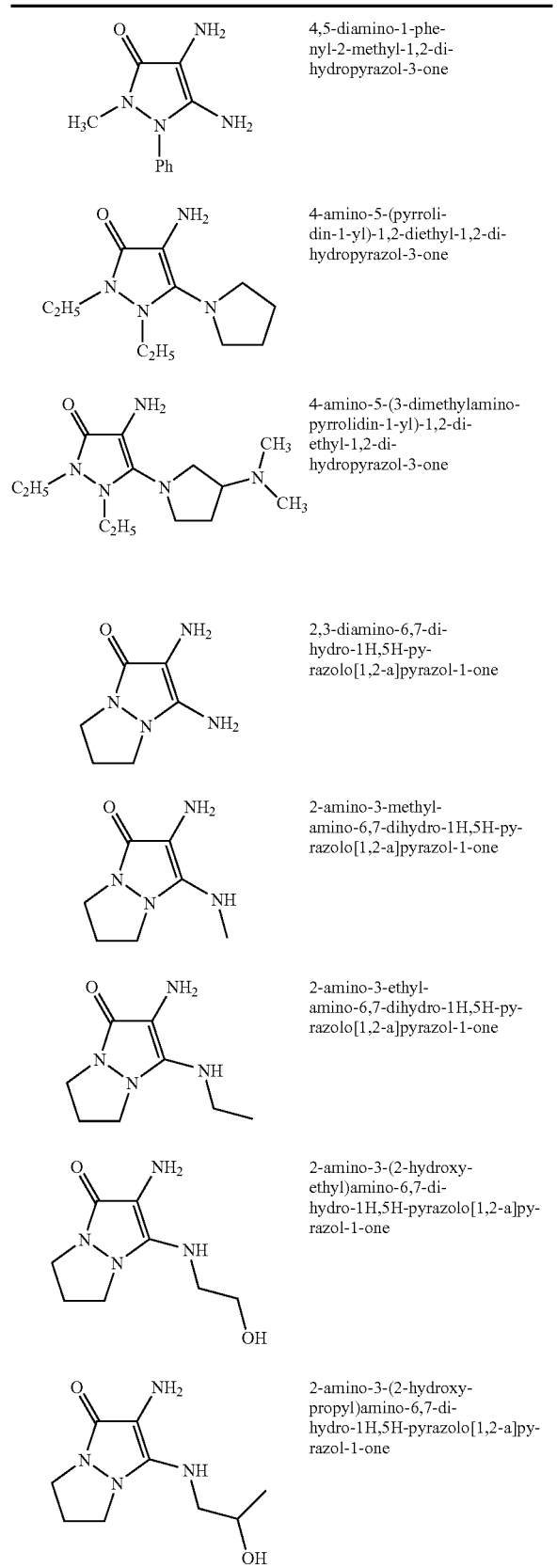
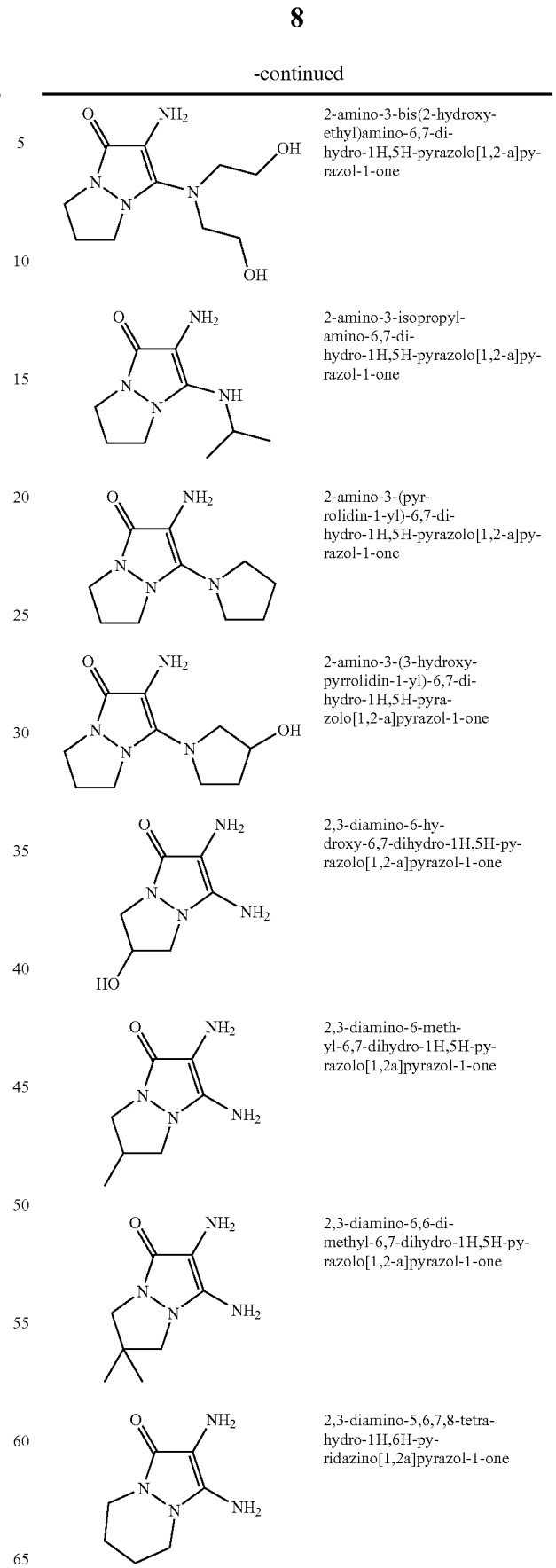

- 4,5-diamino-1-phenyl-2-methyl-1,2-dihydropyrazol-3-one
- 4-amino-5-(pyrrolidin-1-yl)-1,2-diethyl-1,2-dihydropyrazol-3-one
- 4-amino-5-(3-dimethylaminopyrrolidin-1-yl)-1,2-diethyl-1,2-dihydropyrazol-3-one
- 2,3-diamino-6,7-dihydro-1H,5H-pyrazolo[1,2-a]pyrazol-1-one
- 2-amino-3-methylamino-6,7-dihydro-1H,5H-pyrazolo[1,2-a]pyrazol-1-one
- 2-amino-3-ethylamino-6,7-dihydro-1H,5H-pyrazolo[1,2-a]pyrazol-1-one
- 2-amino-3-(2-hydroxyethyl)amino-6,7-dihydro-1H,5H-pyrazolo[1,2-a]pyrazol-1-one
- 2-amino-3-(2-hydroxypropyl)amino-6,7-dihydro-1H,5H-pyrazolo[1,2-a]pyrazol-1-one
- 2-amino-3-bis(2-hydroxyethyl)amino-6,7-dihydro-1H,5H-pyrazolo[1,2-a]pyrazol-1-one
- 2-amino-3-isopropylamino-6,7-dihydro-1H,5H-pyrazolo[1,2-a]pyrazol-1-one
- 2-amino-3-(pyrrolidin-1-yl)-6,7-dihydro-1H,5H-pyrazolo[1,2-a]pyrazol-1-one
- 2-amino-3-(3-hydroxypyrrolidin-1-yl)-6,7-dihydro-1H,5H-pyrazolo[1,2-a]pyrazol-1-one
- 2,3-diamino-6-hydroxy-6,7-dihydro-1H,5H-pyrazolo[1,2-a]pyrazol-1-one
- 2,3-diamino-6-methyl-6,7-dihydro-1H,5H-pyrazolo[1,2a]pyrazol-1-one
- 2,3-diamino-6,6-dimethyl-6,7-dihydro-1H,5H-pyrazolo[1,2-a]pyrazol-1-one
- 2,3-diamino-5,6,7,8-tetrahydro-1H,6H-pyridazino[1,2a]pyrazol-1-one

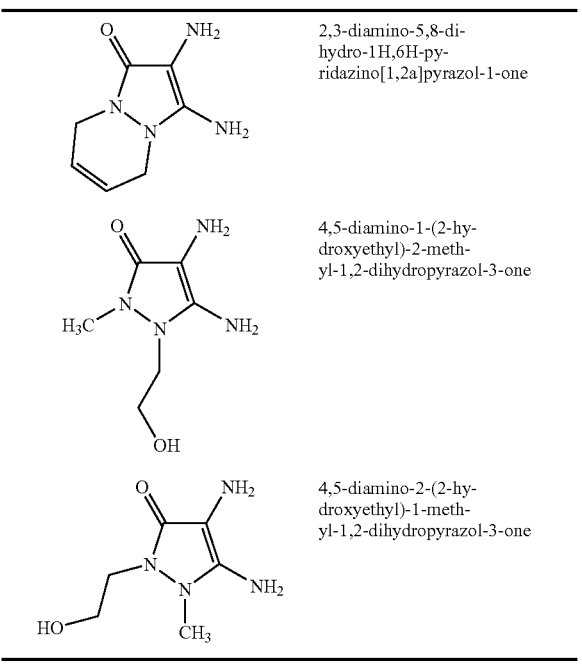

2,3-diamino-5,8-dihydro-1H,6H-pyridazino[1,2a]pyrazol-1-one 4,5-diamino-1-(2-hydroxyethyl)-2-methyl-1,2-dihydropyrazol-3-one 4,5-diamino-2-(2-hydroxyethyl)-1-methyl-1,2-dihydropyrazol-3-one In at least one embodiment, the diamino-N,N-dihydropyrazolone derivatives of formula (I), or the addition salts thereof, may be chosen from:
2,3-diamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
4,5-diamino-1,2-dimethyl-1,2-dihydropyrazol-3-one;
4,5-diamino-1,2-diethyl-1,2-dihydropyrazol-3-one;
4,5-diamino-1,2-di(2-hydroxyethyl)-1,2-dihydropyrazol-3-one;
2-amino-3-(2-hydroxyethyl)amino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
4-amino-1,2-diethyl-5-pyrrolidin-1-yl-1,2-dihydropyrazol-3-one;
4-amino-5-(3-dimethylaminopyrrolidin-1-yl)-1,2-diethyl-1,2-dihydropyrazol-3-one; and
2,3-diamino-6-hydroxy-6,7-dihydro-1H,5H-pyrazolo[1,2-a]pyrazol-1-one.

The at least one oxidation base may be present in the dye composition in an amount ranging from 0.001% to 10% by weight, for example, from 0.005% to 6% by weight, relative to the total weight of the dye composition.

Couplers

The at least one coupler may be chosen, for example, from meta-phenylenediamines, meta-aminophenols, meta-diphenols, naphthalene-based couplers, heterocyclic couplers, and the addition salts thereof.

Examples of suitable couplers include, but are not limited to, 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the acid addition salts thereof.

The at least one coupler may be present (for each coupler) in the dye composition in an amount ranging from 0.001% to 10% by weight, for example, from 0.005% to 6% by weight, relative to the total weight of the dye composition.

Heterocyclic Direct Dyes

As used herein, the term "heterocyclic direct dye" means any direct dye comprising in its structure at least one saturated or unsaturated ring bearing at least one heteroatom chosen from oxygen, sulfur, nitrogen, and phosphorus, optionally fused with a saturated or unsaturated hydrocarbon-based ring. This heterocycle may or may not be substituted and may be charged or uncharged and may or may not comprise at least one carbonyl group.

Examples of such heterocycles include, but are not limited to, thiophene, thianthrene, furan, 1,4-pyran, 1,2-pyran, isobenzofuran, chromene, xanthene, 2H-pyrrole, pyrrole, imidazole, pyrazole, isothiazole, isoxazole, pyridine, pyrazine, pyrimidine, pyridazine, indolizine, isoindole, 3H-indole, indole, 1H-indazole, purine, 4H-quinolizine, isoquinoline, quinoline, phthalazine, naphthyridine, quinoxaline, cinnoline, pteridine, carbazole, 4a,H-carbazole, carboline, phenanthridine, acridine, perimidine, phenanthroline, phenazine, phenothiazine, furazan, phenoxazine, phenoxathine, pyrrolidine, isochroman, chroman, pyrroline, imidazoline, imidazolidine, pyrazoline, pyrazolidine, morpholine, benzisoquinoline, imidazothiazole, benzothiazole, benzofuran, 1,2,3-triazole, 1,2,4-triazole, isoazole, 1,4-oxazine, o- or p-isoxazine, 1,2,5-oxathiazine, 1,2,6-oxathiazine, 1,4,2-oxadiazine, 1,3,5,2-oxadiazine, 3-isopyrrole, indene, isoindene, indoline, isoindoline, 1,2,3,4-oxatriazole, 1,2,3,5-oxatriazole, piperazine, piperidine, 1,3,5-triazine, 1,2,4-triazine, 1,2,3-triazine, 1,3,2-benzoxazine, 1,4,2-benzoxazine, isocoumarin, 1,2,3-dioxazole, 1,2,4-dioxazole, 1,3,2-dioxazole, 1,3,4-dioxazole, 1,2,5-oxathiazole, 1,3-oxathiol, 1,2,3,4-tetrahydroquinoxaline, quinazoline, pyrazolotriazole, thiazole, and indolenine rings, and homologues thereof including at least one carbonyl group, for instance, pyrazolone, indolinedione, 1,2-pyrone, 1,4-pyrone, and quinolinone rings. These rings may be optionally substituted with at least one substituent chosen, for example, from optionally substituted linear or branched $C_1$-$C_{10}$ alkyl, amino, hydroxyl, halogen, linear or branched $C_2$-$C_{10}$ alkenyl, $C_1$-$C_{10}$ mono- or polyhydroxyalkyl, $C_1$-$C_{10}$ mono- or polyaminoalkyl, mono- or di($C_1$-$C_6$)alkylamino, mono- or dihydroxy($C_1$-$C_6$)alkylamino, mono($C_1$-$C_6$)alkylmonohydroxy($C_1$-$C_6$)alkylamino, mono- or di($C_1$-$C_6$)alkylamino($C_1$-$C_{10}$)alkyl, mono- or dihydroxy($C_1$-$C_6$)alkylamino($C_1$-$C_{10}$)alkyl, mono($C_1$-$C_6$)alkylmonohydroxy($C_1$-$C_6$)alkylamino($C_1$-$C_{10}$)alkyl, nitro, carboxyl, carboxy($C_1$-$C_{10}$)alkyl, ($C_1$-$C_6$)alkoxycarbonyl, sulfo, sulfo($C_1$-$C_{10}$)alkyl, ($C_1$-$C_{10}$)alkoxy, ureido, tri($C_1$-$C_6$)alkylammonium, tri($C_1$-$C_6$)alkylammonium($C_1$-$C_{10}$)alkyl, and ($C_8$-$C_{30}$)aryl radicals.

The at least one heterocyclic direct dye may be in the form of a monomer or may be integrated into the repeating units of polymers chosen from nonionic, monoanionic, polyanionic, monocationic, and polycationic polymers.

The at least one heterocyclic dye may be chosen from neutral, acidic, and basic dyes, and the organic portion bearing the chromophore may be neutral or may bear a negative or positive overall charge.

According to one embodiment of the present disclosure, the at least one neutral heterocyclic direct dye may be chosen from those comprising at least one ring chosen from pyridine, quinoxaline, pyrazoline, pyrazole, oxadiazole, thiazole, pyrrole, indole, pyrazolotriazole, quinoline, indoline, phenazine, coumarin, and benzopyran rings, and homologues thereof including at least one carbonyl group.

Non-limiting examples of neutral heterocyclic dyes include 2,5-diamino-6-nitropyridine; 5-amino-2-(2'-hydroxyethyl)amino-6-nitropyridine; 2-amino-5-(2'-hydroxyethyl)amino-6-nitropyridine; 5-amino-2-ethylamino-6-nitropyridine; 2-ethylamino-5-(2'-hydroxyethyl)amino-6-nitropyridine; 2-methylamino-5-(2'-hydroxyethyl)amino-6-nitropyridine; nitroquinoxalines described, for example, in German Patent Application Nos. 3 825 212 and 4 404 564, such as 1,2,3,4-tetrahydro-6-nitroquinoxaline; pyridine compounds described, for example, in French Patent Application No. 2 845 387; compounds comprising pyrazoline rings described, for example, in French Patent Application No. 2 746 392; compounds comprising pyrazole rings described, for example, in German Patent Application No.197 30 412; compounds comprising oxadiazole rings described, for example, in International Patent Application Publication No. WO 2002/22093; compounds comprising thiazole rings described, for example, in German Patent Application No.101 18 271; compounds comprising pyrrole rings described, for example, in French Patent Application No. 2 760 010; compounds comprising indole rings described, for example, in French Patent Application No. 2 978 931; compounds comprising pyrazolotriazole rings described, for example, in German Patent Application No. 201 04 441; compounds comprising quinoline and quinoxaline rings described, for example, in European Patent Application No. 0 984 010; 2,3-indolinedione; Vat Blue 6 (phenazine); Disperse Yellow 184 (coumarin); brasiline; and hematoxylin (benzopyrans).

According to another embodiment of the present disclosure, the at least one anionic heterocyclic direct dye may be chosen from those comprising at least one ring chosen from pyrazole, xanthene, quinoline, benzotriazole, benzoquinoline, indoline, and naphthotriazole rings, and homologues thereof including at least one carbonyl group.

Examples of anionic heterocyclic dyes include, but are not limited to, Acid Yellow 23 (compound comprising a pyrazolone ring), Acid Yellow 73 (compound comprising a xanthene ring), Acid Red 92 (compound comprising a xanthene ring), Acid Yellow 3 (compound comprising a quinoline ring), Food Yellow 4 (compound comprising a pyrazolone ring), Acid Red 51 (compound comprising a benzothiazole ring), Acid Red 52 (compound comprising a xanthene ring), Acid Red 87 (compound comprising a benzoquinoline ring), Acid Red 95 (compound comprising a xanthene ring), Acid Red 92 (compound comprising a xanthene ring), Acid Blue 74 (compound comprising an indolinone ring), Acid Red 195 (compound comprising a pyrazole ring), Acid Orange 92 (compound comprising a pyrazolone ring), Acid Yellow 5 (compound comprising a benzoquinoline ring), Acid Black 70 (compound comprising a quinolinone ring), Direct Yellow 106 (compound comprising a naphthotriazole ring), Direct Yellow 59 (compound comprising a benzothiazole ring), and Acid Yellow 14 (compound comprising a pyrazolone ring).

According to yet another embodiment of the present disclosure, the at least one cationic heterocyclic direct dye may comprise at least one cationic filler belonging to a heterocycle.

According to a further embodiment, the at least one cationic heterocyclic direct dye may be chosen from cationic dyes comprising xanthene rings, cationic dyes comprising acridene rings, cationic dyes comprising benzothiazole rings, cationic dyes comprising phenothiazine rings, cationic dyes comprising pyrazole rings, cationic dyes comprising triazole rings, cationic dyes comprising thiazole rings, cationic dyes comprising phenazine rings, cationic dyes comprising indolenine rings, cationic dyes comprising phenoxazine rings, cationic dyes comprising imidazole rings, cationic dyes comprising pyridine rings, and homologues thereof including at least one carbonyl group.

Non-limiting examples of suitable cationic heterocyclic dyes include, but are not limited to:

cationic dyes comprising xanthene rings, for instance, Basic Red 1, Basic Red 3, Basic Red 4, Basic Violet 10, and Basic Violet 11, cationic dyes comprising acridine rings, for instance, Basic Orange 15, Basic Orange 16, and Basic Orange 17, cationic dyes comprising benzothiazole rings, for instance, Basic Blue 41 and Basic Blue 67, cationic dyes comprising phenothiazine rings, for instance, Basic Blue 9, cationic dyes comprising pyrazolone rings, for instance, Basic Yellow 57, cationic dyes comprising triazole rings, for instance, Basic Red 22 and Basic Red 46, cationic dyes comprising thiazole rings, for instance, Basic Red 29, cationic dyes comprising phenazine rings, for instance, Basic Red 2, cationic dyes comprising indolenine rings, for instance, Basic Red 14, Basic Yellow 13, Basic Yellow 28, and Basic Yellow 29, cationic dyes comprising phenoxazine rings, for instance, Basic Blue 6, dyes described, for example, in European Patent Application No. 1 025 834, for instance:

compounds of formula (II):

$$G-N=N-J \qquad (II)$$

wherein:

the symbol G is a group chosen from formulas $G_1$, $G_2$, and $G_3$:

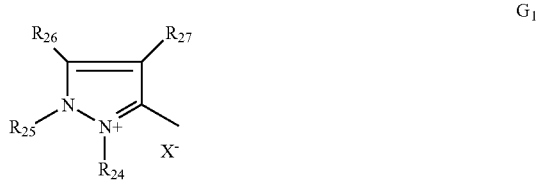

-continued

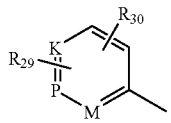

G₃ wherein:
- $R_{24}$ is chosen from $C_1$-$C_4$ alkyl radicals, phenyl radicals which may be substituted with at least one radical chosen from $C_1$-$C_4$ alkyl radicals, and halogen atoms chosen from chlorine, bromine, iodine, and fluorine;
- $R_{25}$ is chosen from $C_1$-$C_4$ alkyl radicals and phenyl radicals;
- $R_{26}$ and $R_{27}$, which may be identical or different, are chosen from $C_1$-$C_4$ alkyl radicals and phenyl radicals, or may form together in $G_1$ a benzene ring substituted with at least one radical chosen from $C_1$-$C_4$ alkyl, $C_1$-$C_4$ alkoxy, and $NO_2$ radicals, or may form together in $G_2$ a benzene ring optionally substituted with at least one radical chosen from $C_1$-$C_4$ alkyl, $C_1$-$C_4$ alkoxy, and $NO_2$ radicals;
- $R_{26}$ may also be hydrogen;
- Z is chosen from oxygen, sulfur, and $-NR_{26}$;
- M is chosen from $-CH$, $-CR$ (wherein R is a $C_1$-$C_4$ alkyl group), and $-NR_{28}(X^-)_r$;
- K is chosen from $-CH$, $-CR$ (wherein R is a $C_1$-$C_4$ alkyl group), and $-NR_{28}(X^-)_r$;
- P is chosen from $-CH$, $-CR$ (wherein R is a $C_1$-$C_4$ alkyl group), and $-NR_{28}(X^-)_r$;
- r is equal to 0 or 1;
- $R_{28}$ is chosen from $O^-$, $C_1$-$C_4$ alkoxy radicals, and $C_1$-$C_4$ alkyl radicals;
- $R_{29}$ and $R_{30}$, which may be identical or different, are chosen from hydrogen, halogen atoms such as chlorine, bromine, iodine, and fluorine, $C_1$-$C_4$ alkyl radicals, $C_1$-$C_4$ alkoxy radicals, and $-NO_2$ radicals;
- $X^-$ is an anion chosen, for example, from chloride, iodide, methyl sulfate, ethyl sulfate, acetate, and perchlorate;
- the symbol J is chosen from:
  (a) groups of formula $J_1$:

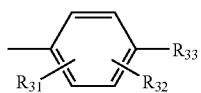

$J_1$ wherein:
- $R_{31}$ is chosen from hydrogen, halogen atoms such as chlorine, bromine, iodine, and fluorine, $C_1$-$C_4$ alkyl radicals, $C_1$-$C_4$ alkoxy radicals, $-OH$ radicals, $-NO_2$ radicals, $-NHR_{34}$ radicals, $-NR_{35}R_{36}$ radicals, and $C_1$-$C_4$—NHCO alkyl radicals, or may form together with $R_{32}$ a 5- or 6-membered ring optionally comprising at least one heteroatom chosen from nitrogen, oxygen, and sulfur;
- $R_{32}$ is chosen from hydrogen, halogen atoms such as chlorine, bromine, iodine, and fluorine, $C_1$-$C_4$ alkyl radicals, $C_1$-$C_4$ alkoxy radicals, or may form, together with $R_{33}$ or $R_{34}$, a 5- or 6-membered ring optionally comprising at least one heteroatom chosen from nitrogen, oxygen, and sulfur;
- $R_{33}$ is chosen from hydrogen, $-OH$ radicals, $-NHR_{34}$ radicals, and $-NR_{35}R_{36}$ radicals;
- $R_{34}$ is chosen from hydrogen, $C_1$-$C_4$ alkyl radicals, $C_1$-$C_4$ monohydroxyalkyl radicals, $C_2$-$C_4$ polyhydroxyalkyl radicals, and phenyl radicals;
- $R_{35}$ and $R_{36}$, which may be identical or different, are chosen from $C_1$-$C_4$ alkyl radicals, $C_1$-$C_4$ monohydroxyalkyl radicals, and $C_2$-$C_4$ polyhydroxyalkyl radicals;

(b) 5- or 6-membered nitrogenous heterocyclic groups, which may optionally comprise at least one entity chosen from heteroatoms and/or carbonyl groups and may be optionally substituted with at least one radical chosen from $C_1$-$C_4$ alkyl, amino, and phenyl radicals, for example, groups of formula $J_2$:

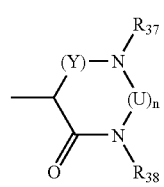

$J_2$ wherein:
- $R_{37}$ and $R_{38}$, which may be identical or different, are chosen from hydrogen, $C_3$-$C_{10}$ alkyl radicals, and phenyl radicals;
- Y is chosen from $-CO-$ radicals and $-C(CH_3)=$ radicals;
- n is equal to 0 or 1, and
- when n is equal to 1, U is a $-CO-$ radical; and wherein when J is chosen from groups of formula $J_1$, at least one of the groups K, P, and M is $NR_{28}(X^-)_r$, compounds of formula (III):

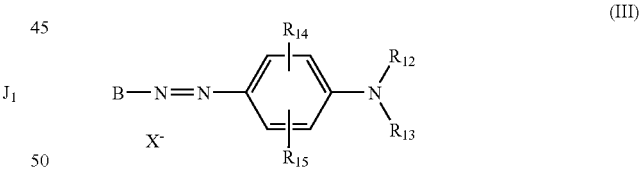

(III)

wherein:
- $R_{12}$ is chosen from hydrogen and $C_1$-$C_4$ alkyl radicals,
- $R_{13}$ is chosen from hydrogen, alkyl radicals which may be optionally substituted with at least one entity chosen from $-CN$ radicals and amino groups, 4'-aminophenyl radicals, or may form, together with $R_{12}$, a heterocycle optionally comprising oxygen and/or nitrogen, which may be substituted with at least one radical chosen from $C_1$-$C_4$ alkyl radicals,
- $R_{14}$ and $R_{15}$, which may be identical or different, are chosen from hydrogen; halogen atoms such as bromine, chlorine, iodine, and fluorine; $C_1$-$C_4$ alkyl radicals; $C_1$-$C_4$ alkoxy radicals; and $-CN$ radicals, X⁻ is an anion chosen, for example, from chloride, methyl sulfate, and acetate, B is chosen from groups of formulas B1 to B6:

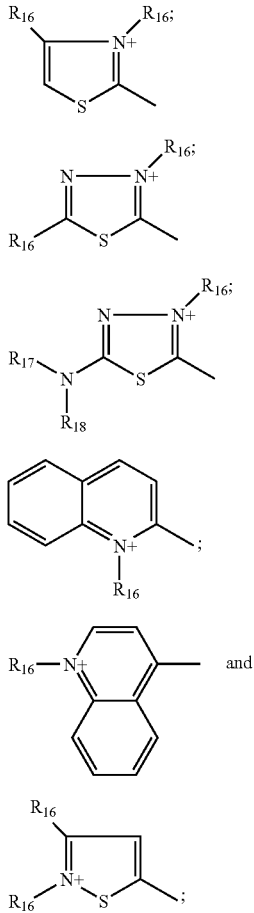

wherein:
R$_{16}$ is chosen from C$_1$-C$_4$ alkyl radicals,
R$_{17}$ and R$_{18}$, which may be identical or different, are chosen from hydrogen and C$_1$-C$_4$ alkyl radicals,
compounds of formulae (IV) and (V):

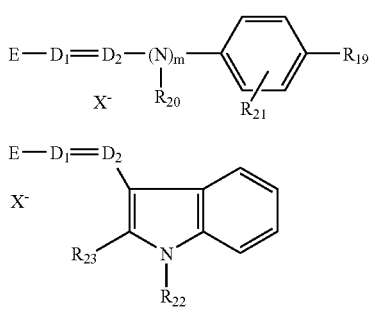

wherein:
R$_{19}$ is chosen from hydrogen, C$_1$-C$_4$ alkoxy radicals, halogen atoms such as bromine, chlorine, iodine, and fluorine, and amino radicals, R$_{20}$ is chosen from hydrogen and C$_1$-C$_4$ alkyl radicals, or may form, together with a carbon atom of the benzene ring, a heterocycle optionally comprising oxygen and/or substituted with at least one C$_1$-C$_4$ alkyl group, R$_{21}$ is chosen from hydrogen and halogen atoms such as bromine, chlorine, iodine, and fluorine, R$_{22}$ and R$_{23}$, which may be identical or different, are chosen from hydrogen and C$_1$-C$_4$ alkyl radicals, D$_1$ and D$_2$, which may be identical or different, are chosen from hydrogen and —CH, m is equal to 0 or 1, with the proviso that when R$_{19}$ is an unsubstituted amino group, then D$_1$ and D$_2$ are —CH and m is equal to 0, X⁻ is an anion chosen from chloride, methyl sulfate, and acetate, E is chosen from groups of formulas E1 to E8:

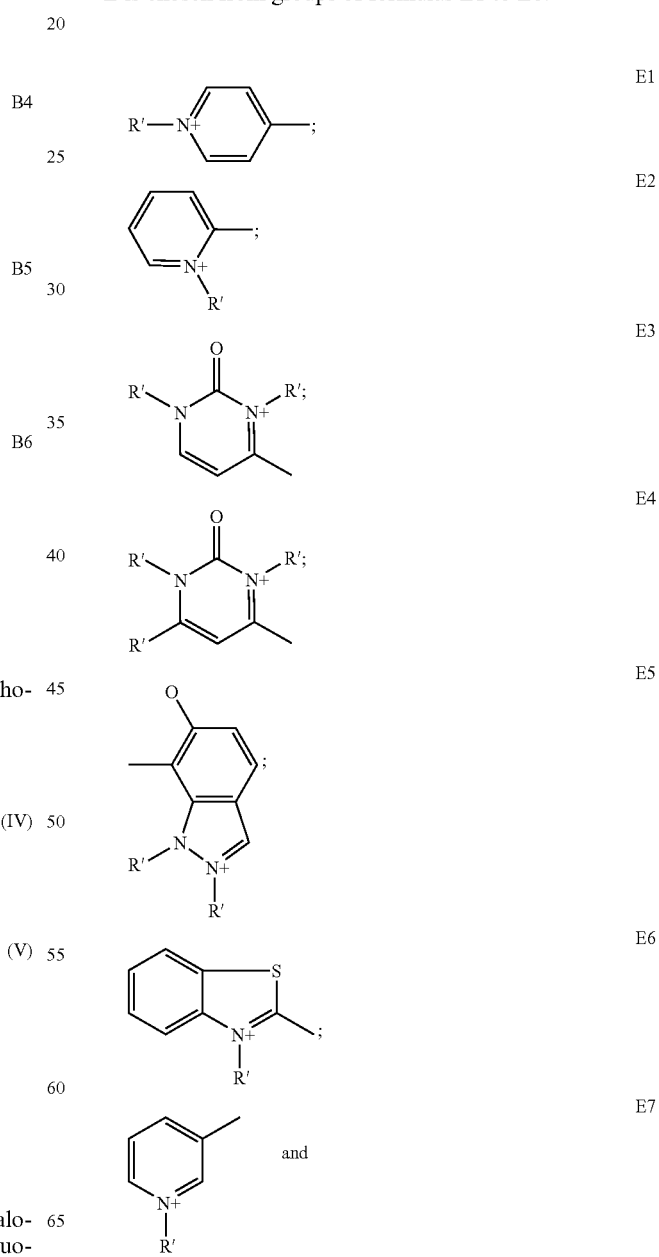

-continued

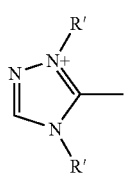
E8 in which R' is chosen from $C_1$-$C_4$ alkyl radicals; and when m is equal to 0 and $D_1$ is nitrogen, then E may also be chosen from group E9:

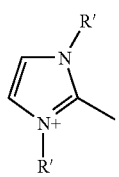
E9 in which R' is chosen from $C_1$-$C_4$ alkyl radicals; and compounds of formula (VI):

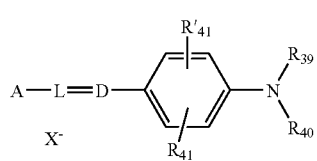
(VI)

wherein:
L and D, which may be identical or different, are chosen from nitrogen and —CH,
$R_{39}$ and $R_{40}$, which may be identical or different, are chosen from hydrogen; $C_1$-$C_4$ alkyl radicals which may be optionally substituted with at least one radical chosen from —CN, —OH, and —NH$_2$ radicals, or may form, together with a carbon atom of the benzene ring, a heterocycle optionally comprising at least one entity chosen from oxygen and nitrogen, which may be optionally substituted with at least one $C_1$-$C_4$ alkyl radical; and 4'-aminophenyl radicals,
$R_{41}$ and $R'_{41}$, which may be identical or different, are chosen from hydrogen, halogen atoms such as chlorine, bromine, iodine, and fluorine, cyano radicals, $C_1$-$C_4$ alkyl radicals, $C_1$-$C_4$ alkoxy radicals, and acetyloxy radicals,
X⁻ is an anion chosen, for example, from chloride, methyl sulfate, and acetate,
A is chosen from groups of formulas $A_1$ to $A_{19}$:

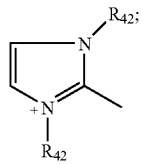
$A_1$

-continued

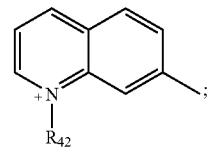
$A_2$

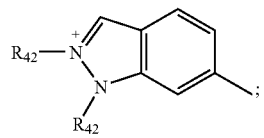
$A_3$

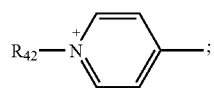
$A_4$

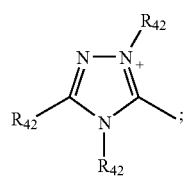
$A_5$

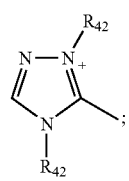
$A_6$

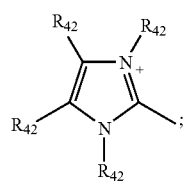
$A_7$

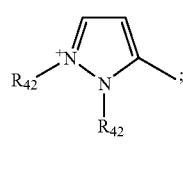
$A_8$

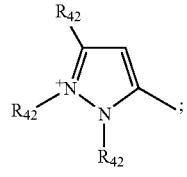
$A_9$

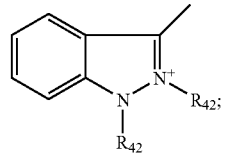
$A_{10}$

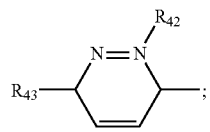
$A_{11}$

-continued

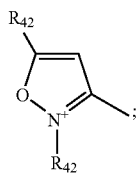 $A_{12}$

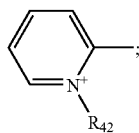 $A_{13}$

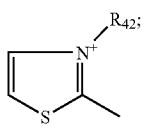 $A_{14}$

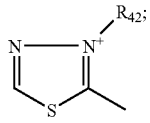 $A_{15}$

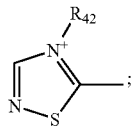 $A_{16}$

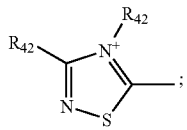 $A_{17}$

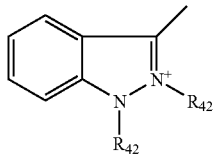 and $A_{18}$

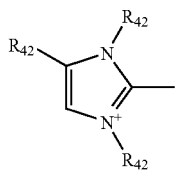 $A_{19}$ wherein:
$R_{42}$ is chosen from $C_1$-$C_4$ alkyl radicals which may be substituted with at least one hydroxyl radical; and
$R_{43}$ is chosen from $C_1$-$C_4$ alkoxy radicals,
dyes described in European Patent Application No. 0 714 954, for example, compounds of formulae (VII), (VIII), and (IX):

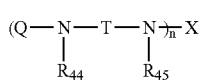 (VII)

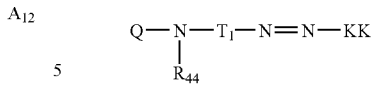 (VIII)

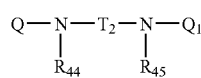 (IX)

wherein:
Q and $Q_1$, which may be identical or different, are chosen from residues of the following formula:

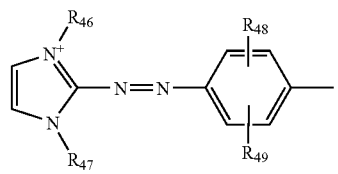

T is chosen from aliphatic and aromatic diamines,
$R_{44}$ and $R_{45}$, which may be identical or different, are chosen from hydrogen and $C_1$-$C_4$ alkyl groups, or may form, together with two nitrogen atoms to which they are attached, or with T and $T_2$, a 5-, 6-, or 7-membered ring,
X is chosen from residues of chain units forming a bridge,
n is an integer ranging from 2 to 4
$T_1$ is chosen from aromatic diamine residues,
$T_2$ is chosen from aliphatic diamine residues,
KK is chosen from coupling compound residues,
$R_{46}$ and $R_{47}$, which may be identical or different, are chosen from hydrogen and $C_1$-$C_4$ alkyl groups,
$R_{48}$ and $R_{49}$, which may be identical or different, are chosen from hydrogen, $C_1$-$C_4$ alkyl groups, and $C_1$-$C_4$ alkoxy groups, and
An- is a colorless anion, and
cationic dyes described in International Patent Application Publication Nos. WO 95/01772 and WO 95/15144 and European Patent Nos. 0 714 954, 1 170 000, 1 166 753, 1 166 754, and 1 170 001, which are different from the above dyes, and which are incorporated herein by reference.

In at least one embodiment, the at least one heterocyclic direct dye may be chosen from Basic Red 51 of formula (X):

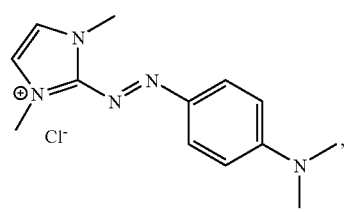 (X)

Basic Yellow 87 of formula (XI):

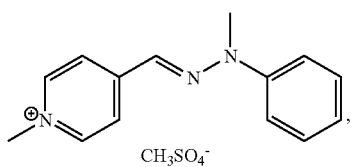

(XI)

and Basic Orange 31 of formula (XII):

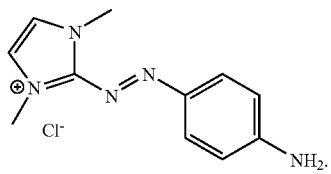

(XII)

In another embodiment, the at least one heterocyclic direct dye may be a cationic direct dye.

It is to be understood that, in the context of the present disclosure, the dyes as described above and the mesomeric forms thereof, and also, in the context of charged dyes, dyes that differ from those mentioned only in the nature of the counterion(s), may also be used as direct dyes in accordance with the present disclosure.

The at least one heterocyclic direct dye may be present in the composition in an amount (for each heterocyclic dye) ranging from 0.0001% to 30% by weight, for example, from 0.001% and 20% by weight, or from 0.01% to 15% by weight, relative to the total weight of the composition.

The dye composition of the present disclosure may further comprise oxidation bases other than the compounds of formula (I), which may be chosen from those conventionally used for the dyeing of keratin fibers.

The composition of the present disclosure may comprise, for example, at least one additional oxidation base chosen from para-phenylenediamines, bis(phenyl)alkylenediamines, para-aminophenols, bis-para-aminophenols, ortho-aminophenols, ortho-phenylenediamines, and heterocyclic bases other than the compounds of formula (I), and the addition salts thereof.

Examples of suitable para-phenylenediamines include, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenyl-enediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxy-propyl)-para-phenylenediamine, N-(4'-aminophenyl)-para-phenylenediamine, N-phenyl-para-phenylenediamine, 2-β-hydroxyethyloxy-para-phenylenediamine, 2-β-acetylamino-ethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the acid addition salts thereof.

In at least one embodiment, the para-phenylenediamines may be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts thereof.

Non-limiting examples of suitable bis(phenyl)alkylenediamines include N,N'-bis(β-hydroxyethyl)-N,N'-bis(4'-aminophenyl)-1,3-diaminopropanol, N,N'-bis-(β-hydroxyethyl)-N,N'-bis(4'-aminophenyl)ethylenediamine, N,N'-bis(4-aminophenyl)tetra-methylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the acid addition salts thereof.

Suitable para-aminophenols include, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the acid addition salts thereof.

Ortho-aminophenols may be chosen, for example, from 2-aminophenol, 2-amino-5-methylphenol, 2-amino-6-methylphenol, 5-acetamido-2-aminophenol, and the acid addition salts thereof.

Examples of heterocyclic bases, include, but are not limited to, pyridine derivatives, pyrimidine derivatives, and pyrazole derivatives.

Non-limiting examples of pyridine derivatives include the compounds described, for example, in British Patent Nos. 1 026 978 and 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and the acid addition salts thereof.

Further examples of suitable pyridine oxidation bases include, but are not limited to, 3-aminopyrazolo[1,5-a]pyridine oxidation bases or the addition salts thereof described, for example, in French Patent Application No. 2 801 308, for example, pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid, 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2,3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-yl-pyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino]ethanol; 2-[(3-aminopyrazolo[1,5-a]pyrid-7-yl)(2-hydroxyethyl)amino]ethanol; 3-aminopyrazolo[1,5-a]pyrid-5-ol;

3-aminopyrazolo[1,5-a]pyrid-4-ol; 3-aminopyrazolo[1,5-a]pyrid-6-ol; 3-aminopyrazolo[1,5-a]pyrid-7-ol; and the acid and base addition salts thereof.

Suitable pyrimidine derivatives include, for instance, the compounds described, for example, in German Patent No. 2 359 399, Japanese Patent Application No. 88-169 571; Japanese Patent No. 05 63 124; European Patent No. 0 770 375, and International Patent Application No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, and 2,5,6-triaminopyrimidine; and pyrazolopyrimidine derivatives such as those mentioned in French Patent Application No. 2 750 048, for example, pyrazolo[1,5-a]-pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, the acid addition salts thereof, and the tautomeric forms thereof, when a tautomeric equilibrium exists.

Examples of pyrazole derivatives include, but are not limited to, the compounds described in German Patent Nos. 195 43 988, 3 843 892, and 4 133 957, International Patent Application Publication Nos. WO 94/08969 and WO 94/08970, and French Patent Application No. 2 733 749, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, and 3,5-diamino-4-(β-hydroxyethyl)amino-1-methylpyrazole, and the acid addition salts thereof.

The at least one additional oxidation base may be present in the dye composition in an amount (of each additional oxidation base) ranging from 0.001% to 10% by weight relative to the total weight of the dye composition, for example, from 0.005% to 6% by weight.

The addition salts of the oxidation bases and of the couplers that may be used in accordance with the present disclosure may be chosen, for example, from the acid addition salts, such as the hydrochlorides, hydrobromides, sulfates, citrates, succinates, tartrates, lactates, tosylates, benzenesulfonates, phosphates, and acetates, and the base addition salts, such as sodium hydroxide, potassium hydroxide, ammonia, amines, and alkanolamines.

The medium that is suitable for dyeing, also known as the dye support, is a cosmetic medium chosen from water and mixtures of water and at least one organic solvent to dissolve the compounds which would not be sufficiently soluble in water. Examples of suitable organic solvents, include, but are not limited to, $C_1$-$C_4$ lower alkanols, such as ethanol and isopropanol; polyols and polyol ethers such as 2-butoxyethanol, propylene glycol, propylene glycol monomethyl ether, diethylene glycol monoethyl ether, and monomethyl ether; aromatic alcohols such as benzyl alcohol and phenoxyethanol; and mixtures thereof.

The at least one solvent may be present in the dye composition in an amount ranging from 1% to 40% by weight relative to the total weight of the dye composition, for example, from 5% and 30% by weight.

The dye composition in accordance with the present disclosure may also contain at least one adjuvant conventionally used in compositions for dyeing the hair, such as anionic, cationic, nonionic, amphoteric, or zwitterionic surfactants and mixtures thereof; anionic, cationic, nonionic, amphoteric, or zwitterionic polymers and mixtures thereof; inorganic or organic thickeners, such as anionic, cationic, nonionic, and amphoteric associative polymeric thickeners; antioxidants; penetrants; sequestrants; fragrances; buffers; dispersants; conditioning agents, for instance, silicones, which may be volatile or non-volatile, and modified or unmodified; film-forming agents; ceramides; preserving agents; and opacifiers.

The at least one adjuvant may be present in the dye composition in an amount ranging from 0.01% to 20% by weight relative to the total weight of the dye composition.

It is to be understood that a person skilled in the art will take care to select the optional additional compounds such that the beneficial properties intrinsically associated with the oxidation dye composition in accordance with the present disclosure are not, or are not substantially, adversely affected by the addition envisaged.

The pH of the dye composition may range from 3 to 12, for example, from 5 to 11. The pH may be adjusted to the desired value using acidifying or basifying agents conventionally used in the dyeing of keratin fibers, or alternatively, using standard buffer systems.

Examples of acidifying agents include, but are not limited to, inorganic or organic acids such as hydrochloric acid; orthophosphoric acid; sulfuric acid; carboxylic acids such as acetic acid, tartaric acid, citric acid, and lactic acid; and sulfonic acids.

Suitable basifying agents include, for example, aqueous ammonia, alkaline carbonates, alkanolamines such as mono-, di- and triethanolamine and derivatives thereof, sodium hydroxide, potassium hydroxide, and compounds of formula (XIII):

(XIII)

wherein:
W is a propylene residue which is unsubstituted or substituted with at least one radical chosen from hydroxyl and $C_1$-$C_4$ alkyl radicals; and
$R_a$, $R_b$, $R_c$, and $R_d$, which may be identical or different, are chosen from hydrogen, $C_1$-$C_4$ alkyl radicals, and $C_1$-$C_4$ hydroxyalkyl radicals.

The dye composition according to the present disclosure may be in various forms, such as liquids, creams, and gels, and any other form that is suitable for dyeing keratin fibers, such as human hair.

Also disclosed herein is a method for dyeing keratin fibers comprising applying a composition according to the present disclosure to the keratin fibers, and developing the color by applying an oxidizing agent. The color may be developed at acidic, neutral, or alkaline pH and the oxidizing agent may be added to the composition of the present disclosure just at the time of use, or it may be used starting with an oxidizing composition comprising it, which may be applied simultaneously or sequentially to the composition of the present disclosure. In at least one embodiment, the coloration may be developed at neutral pH.

According to one embodiment, the composition of the present disclosure may be is mixed, for example, at the time of use, with a composition comprising, in a medium that is suitable for dyeing, at least one oxidizing agent, this oxidizing agent being present in an amount that is sufficient to develop a desired coloration. The mixture obtained may then be applied to the keratin fibers. After an action time ranging from 3 to 50 minutes, for example, from 5 to 30 minutes, the keratin fibers may be rinsed, washed with shampoo, rinsed again, and then dried.

The oxidizing agents conventionally used for the oxidation dyeing of keratin fibers include, for example, hydrogen peroxide; urea peroxide; alkali metal bromates; persalts such as perborates and persulfates; peracids; and oxidase enzymes, for example, peroxidases, 2-electron oxidoreductases such as uricases, and 4-electron oxygenases, for instance, laccases. In at least one embodiment, the at least one oxidizing agent may be hydrogen peroxide.

The oxidizing composition may also contain at least one adjuvant conventionally used in compositions for dyeing the hair, chosen, for example, from the adjuvants described above.

The pH of the oxidizing composition comprising the at least one oxidizing agent may be such that, after mixing with the dye composition, the pH of the resulting composition applied to the keratin fibers may range from 3 to 12, for example, from 5 to 11. The pH may be adjusted to the desired value by means of acidifying or basifying agents conventionally used in the dyeing of keratin fibers and as described above.

The ready-to-use composition that is finally applied to the keratin fibers may be in various forms, such as liquids, creams, and gels, and any other form that is suitable for dyeing keratin fibers, such as human hair.

Further disclosed herein is a multi-compartment dyeing device or "kit", comprising at least two compartments, in which at least one first compartment contains a dye composition of the present disclosure with the exception of the oxidizing agent, and at least one second compartment contains an oxidizing composition. This device may be equipped with an applicator for applying the desired mixture to the hair, such as the devices described in French Patent No. 2 586 913.

The diamino-N,N-dihydropyrazolone compounds of formula (I) may be obtained from synthetic intermediates and by synthetic routes described in the literature, for example, J. Het. Chem., 38(3): 613-616 (2001), Helvetica Chimica Acta, 33: 1183-1194 (1950), J. Org. Chem., 23: 2029 (1958), J. Am. Chem. Soc., 73: 3240 (1951), J. Am. Chem. Soc., 84: 590 (1962), Justus Liebig Ann. Chem., 686: 134 (1965), Tetrahedron. Lett., 31: 2859-2862 (1973), U.S. Pat. Nos. 4,128,425 and 2,841,584, and the references cited therein.

According to these references, the compounds of formula (I) in which the radicals $R_3$ and $R_4$ are hydrogen atoms may be obtained via the synthetic route represented by scheme A below:

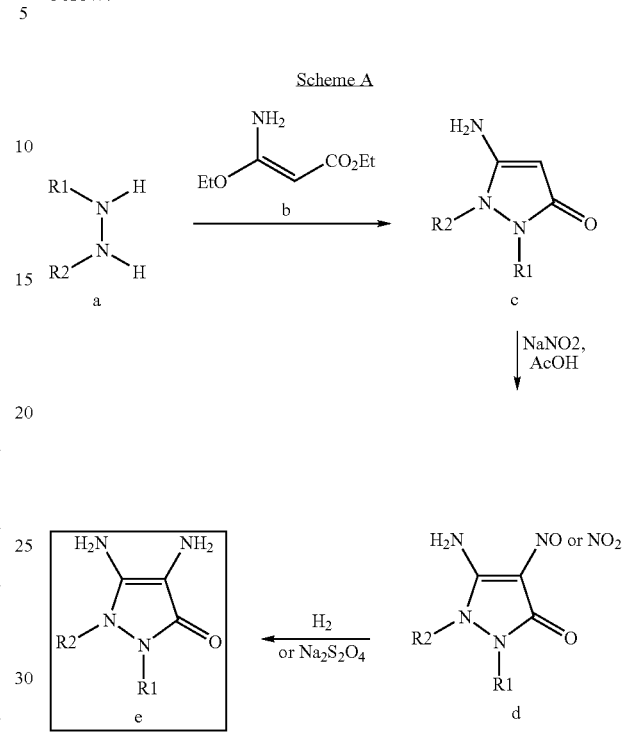

The compounds in which the radicals $R_1$ and $R_2$ are methyl groups and the radicals $R_3$ and $R_4$ are hydrogen atoms may be obtained on the basis of the method described in Justus Lieb. Ann. Chem., 686: 134 (1965) (Scheme B):

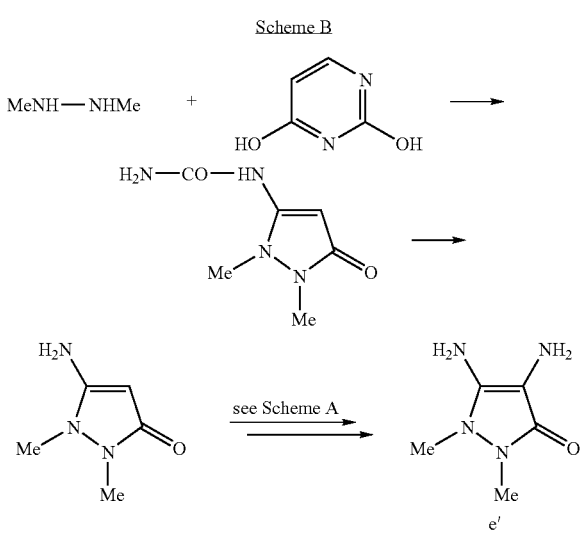

The compounds in which the radical $R_1$ is a methyl group, $R_2$ is a phenyl radical, and the radicals $R_3$ and $R_4$ are hydrogen atoms may be obtained on the basis of the method described in J. Org. Chem., 23: 2029 (1958) and J. Am. Chem. Soc., 73: 3240 (1951) (Scheme C):

Scheme C
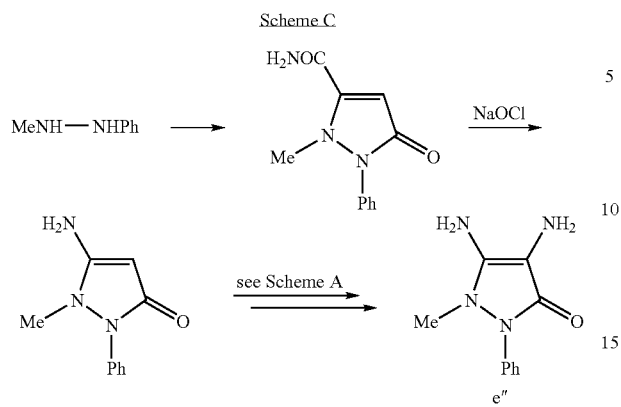
Scheme D
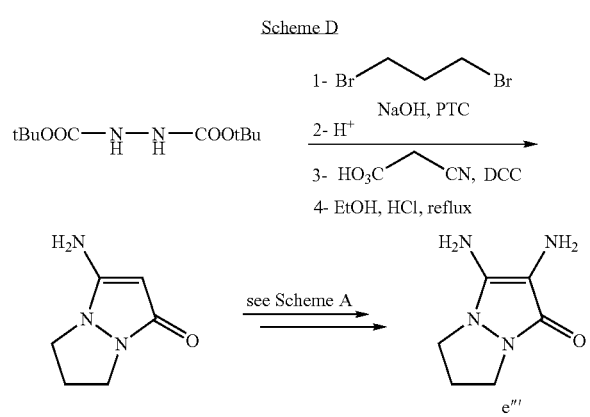
The compounds in which the radicals $R_1$ and $R_2$ together form a 5-membered ring and in which the radicals $R_3$ and $R_4$ are hydrogen atoms may be obtained on the basis of the method described in *J. Het. Chem.*, 38(3): 613-616 (2001) (Scheme D):
According to a different process, the compounds of formula (I) may be obtained according to the synthesis illustrated in Scheme E:
Scheme E
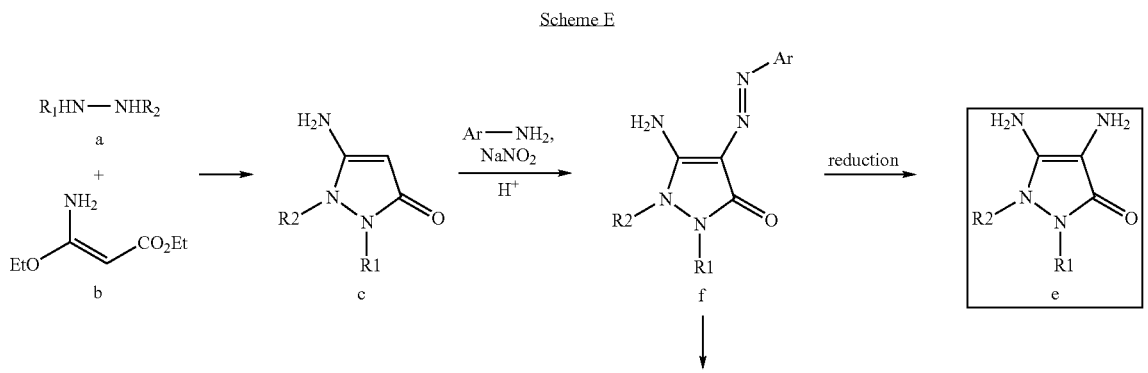
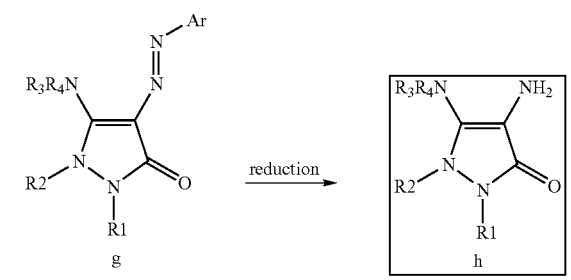

According to this process, the following steps are performed:

a) Step 1: compound a

   a is reacted with compound b:

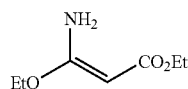   b to obtain a 5-amino-1,2-dihydropyrazol-3-one (compound c):

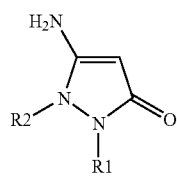   c b) Step 2: the derivative c thus obtained is reacted with an aryldiazonium salt ($ArNH_2$, $NaNO_2$, $H^+$) to obtain azo compound f:

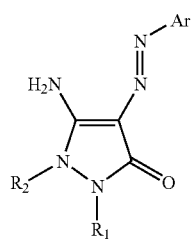   f c) Step 3: a step of functionalization of the primary amine group of the resulting azo compound f is optionally performed to obtain compound g below:

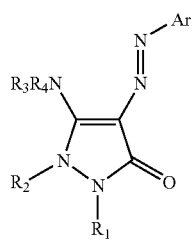   g d) Step 4: a reduction reaction of the azo compound f or g is performed to obtain, respectively, amino compound e or h:

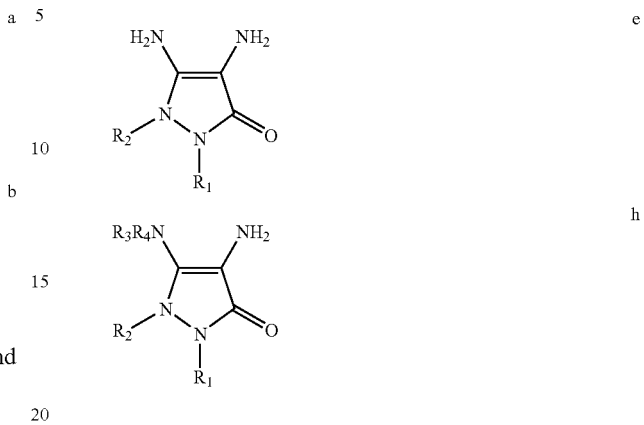

The optional step of functionalization of the primary amine group in position 5 to a secondary and tertiary amine $NR_3R_4$, to obtain compound g, may be performed according to the standard methods of organic synthesis (alkyl halide, alkyl O-sulfonate, alkyl trialkylammonium, reductive amination, etc., see, for example, J. March, *Advanced Organic Chemistry*, 3rd edition, Wiley Interscience (1985)).

Reduction of the azo group leads to compounds e and h in accordance with the present disclosure.

The reduction step may be performed in a conventional manner, for example, by performing a hydrogenation reaction via heterogeneous catalysis in the presence of Pd/C, Pd(II)/C, Ni/Ra, etc., or alternatively, by performing a reduction reaction with a metal, for example, with zinc, iron, tin, etc. (see, for example, J. March, *Advanced Organic Chemistry*, 3rd edition, Wiley Interscience (1985) and M. Hudlicky, *Reduction in Organic Chemistry*, Ellis Horwood Series Chemical Science (1983)).

According to another process, the 2,3-diamino-6,7-dihydro-1H,5H-pyrazolo[1,2-a]pyrazol-1-one and 2,3-diamino-5,6,7,8-tetrahydro-1H,6H-pyridazino[1,2-a]-pyrazol-1-one derivatives may be obtained according to the synthesis illustrated by Scheme F:

Scheme F

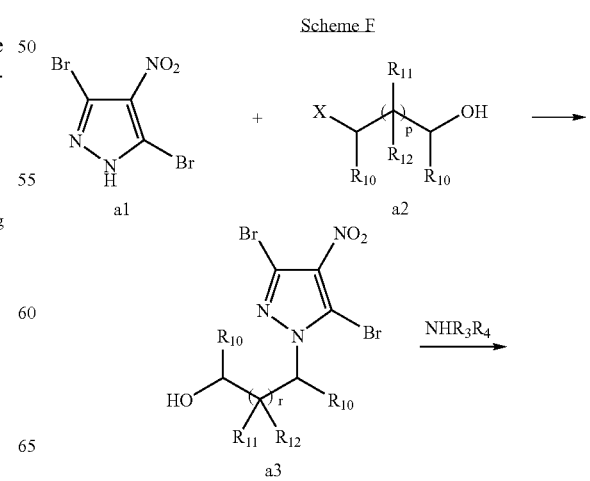

-continued

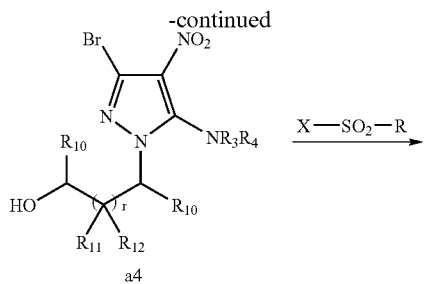
a4

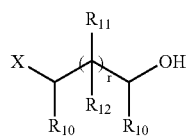
a2 to obtain compound a3:

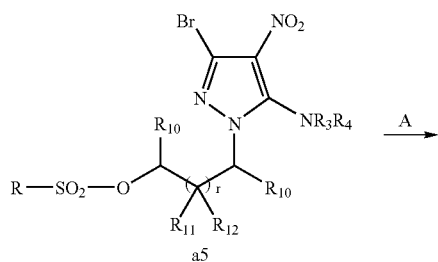
a5

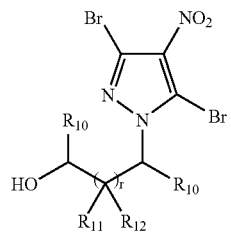
a3 wherein:
the radical $R_{10}$ is chosen from hydrogen; carboxyl radicals; carboxamido radicals; and $C_1$-$C_4$ alkyl radicals optionally substituted with at least one radical chosen from hydroxyl, amino, (di)alkylamino, alkoxy, carboxyl, and sulfonyl radicals;

the radicals $R_{11}$ and $R_{12}$, which may be identical or different, are chosen from hydrogen; halogen atoms; amino radicals; (di)($C_1$-$C_4$)alkylamino radicals; hydroxyl radicals; carboxyl radicals; carboxamido radicals; ($C_1$-$C_2$) alkoxy radicals; $C_1$-$C_4$ alkyl radicals optionally substituted with at least one radical chosen from hydroxyl, amino, (di)alkylamino, alkoxy, carboxyl, and sulfonyl radicals;

X is chosen from halogen atoms and alkylsulfonates; and r is an integer ranging from 1 to 3.

b) Step 2: compound a3 is reacted with an amine of formula $NHR_3R_4$ to obtain compound a4:

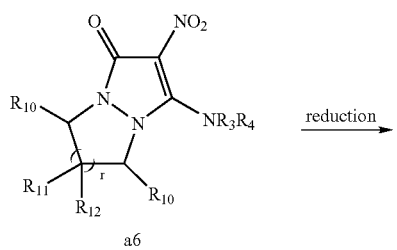
a6

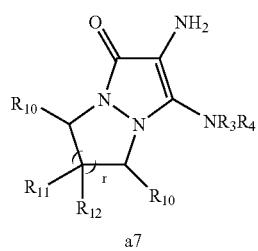
a7

According to this process, the following steps are performed:
a) Step 1: compound a1:

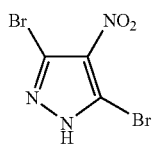
a1 is reacted with compound a2:

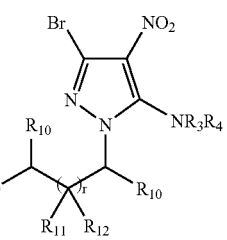
a4 c) Step 3: compound a4 is reacted with at least one halide chosen from alkylsulfonyl, arylsulfonyl, and perfluoroalkylsulfonyl halides R—$O_2$S—$X_1$ (wherein R is chosen from alkyl, aryl, and perfluoroalkyl groups, and $X_1$ is chosen from halogen atoms), in a solvent with a boiling point ranging from 60° C. to 190° C., to obtain compound a5:

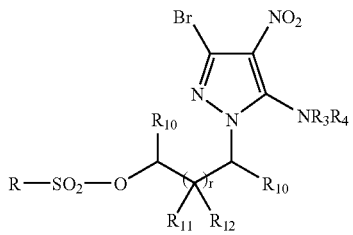

d) Step 4: the resulting compound a5 is then heated in a solvent with a boiling point ranging from 60° C. to 190° C. to obtain compound a6:

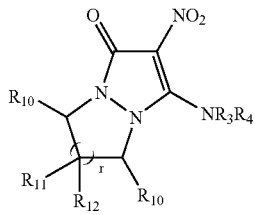

e) Step 5: compound a6 obtained is reduced to obtain compound a7 of formula (XIV):

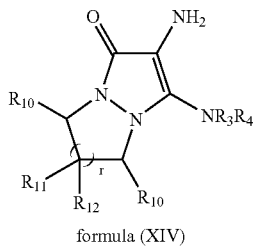

formula (XIV)

In one embodiment, according to this process, the 3,5-dibromo-4-nitropyrazole a1, obtained, for example, according to the method described in German Patent No. 4 234 885, reacts with the reagent a2, for example, in a solvent with a boiling point ranging from 60° C. to 190° C. Examples of suitable solvents include, but are not limited to, pentanol, dimethylformamide, and N-methylpyrrolidine. The reaction may be performed in the presence of an organic or mineral base, for instance, sodium carbonate, sodium hydroxide, sodium acetate, and triethylamine. The temperature of the reaction medium may be maintained at a temperature ranging from 60° C. to 160° C., for example, from 80° C. to 120° C.

The 1-hydroxyalkyl-3,5-dibromo-4-nitropyrazole a3 may be isolated by precipitation or crystallization after addition of ice to the reaction medium.

In step 2, the derivative a3 is reacted with an amine $NHR_3R_4$, for example, in a solvent with a boiling point ranging from 60° C. to 190° C., for instance, butanol, pentanol, range from 60° C. to 160° C., for example, from 80° C. to 120° C. After consumption of the reagents, the 5-amino-4-nitro-3-bromo-1-hydroxyalkylpyrazole compound a4 may be isolated by precipitation or crystallization from water.

In accordance with step 3, the derivative a5 is obtained by reacting the alcohol a4 and a halide chosen from alkylsulfonyl, arylsulfonyl, and perfluoroalkylsulfonyl halides. The reaction may take place in an aprotic solvent, for instance, tetrahydrofuran and dioxane. The reaction temperature may range from −20° C. to 60° C., for example, from 0° C. to 25° C. Furthermore, this step may take place in the presence of an organic or mineral base, for instance, potassium carbonate, triethylamine, and N-methylmorpholine. After disappearance of the reagents, compound a5 may be isolated by precipitation or crystallization from water.

The sulfonate a5 obtained after step 3 is placed, in step 4, in solution or in dispersion in a solvent with a boiling point ranging from 60° C. to 190° C., for example, from 90° C. to 140° C. The reaction medium is then brought to a temperature ranging from 90° C. to 140° C., for example, from 105° C. to 125° C., until all of the sulfonate a5 has been consumed. After cooling to room temperature, the perhydropyrazolo[1,2-a]pyrazol-1-one (r=1), perhydropyridazino[1,2-a]pyrazol-1-one (r=2), or perhydrodiazepino[1,2-a]pyrazolone (r=3) compound a6 crystallizes and may be isolated via the standard methods of organic synthesis.

The final compound a7 in accordance with the present disclosure is obtained, during step 5, via reduction of the nitro derivative a6, the reduction methods used being, for example, a hydrogenation via heterogeneous catalysis in the presence of Pd/C, Pd(II)/C, Ni/Ra, etc., or alternatively, a reduction reaction with a metal, for example with zinc, iron, tin, etc. (see, for example, J. March, *Advanced Organic Chemistry*, 3rd edition, Wiley Interscience (1985) and M. Hudlicky, *Reduction in Organic Chemistry*, Ellis Horwood Series Chemical Science (1983)).

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the present disclosure are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below.

EXAMPLES

Synthesis Examples

Example 1

Synthesis of 2,3-diamino-6,7-dihydro-1H,5H-pyrazolo[1,2-a]pyrazol-1-one dihydrochloride (Compound 5)

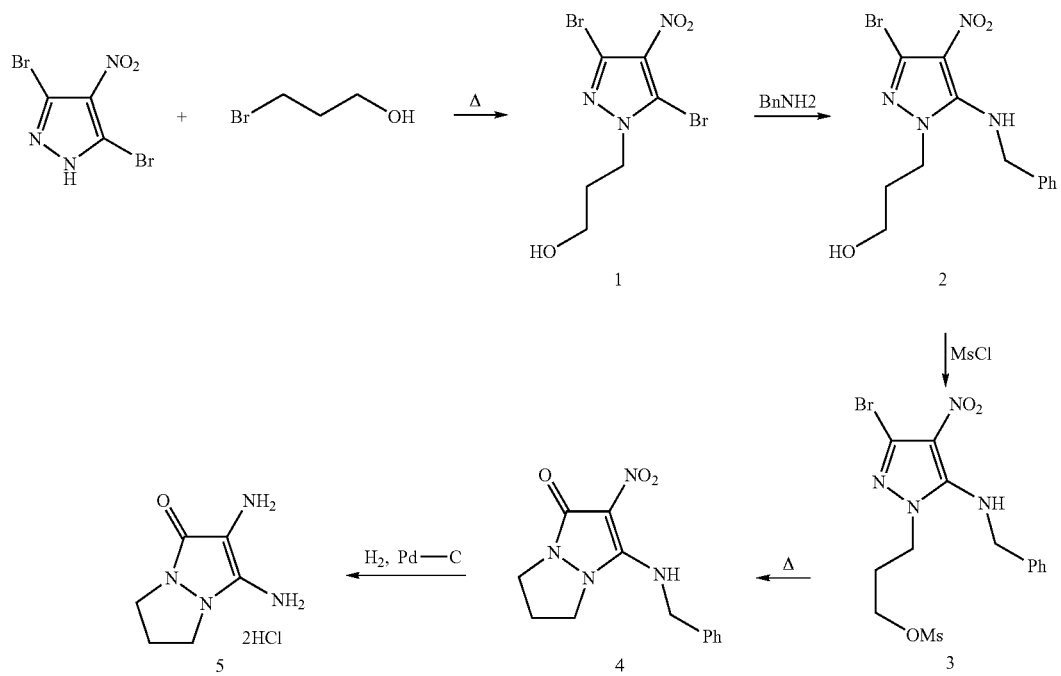

Step 1: Synthesis of 3-(3,5-dibromo-4-nitro-1H-pyrazol-1-yl)propan-1-ol (Compound 1)

0.369 mol of sodium acetate was introduced into a solution of 0.184 mol of dibromonitropyrazole in 250 ml of N-methylpyrrolidone in a 500 ml three-necked flask, and the reaction medium was brought to 80° C.

0.369 mol of 3-bromopropanol was added dropwise at this temperature. This temperature was maintained for 5 hours.

After cooling to room temperature, the medium was poured onto ice with stirring.

The 3-(3,5-dibromo-4-nitro-1H-pyrazol-1-yl)propan-1-ol (compound 1) precipitated. It was filtered off by suction, dried, and obtained in a yield of 75%.

The mass of the expected compound $C_6H_7Br_2N_3O_3$ was detected by mass spectrometry.

The NMR analyses ($^1$H 400 MHz and $^{13}$C 100.61 MHz DMSO $d_6$) were in accordance with the expected structure.

Step 2: Synthesis of 3-[5-(benzylamino)-3-bromo-4-nitro-1H-pyrazol-1-yl]propan-1-ol (Compound 2)

0.135 mol of 3-(3,5-dibromo-4-nitro-1H-pyrazol-1-yl)propan-1-ol (compound 1) was dispersed in a 500 ml three-necked flask containing 150 ml of ethanol, the mixture was heated to 60° C. and 0.825 mol of benzylamine was then added over 30 minutes.

After 6 hours at 60° C., the reaction medium was cooled to room temperature.

The 3-[5-(benzylamino)-3-bromo-4-nitro-1H-pyrazol-1-yl]propan-1-ol (compound 2) was precipitated by pouring the reaction medium onto 1 liter of ice with stirring. After filtration by suction and drying under vacuum in the presence of $P_2O_5$, compound 2 was isolated in a yield of 90%.

The NMR analyses ($^1$H 400 MHz and $^{13}$C 100.61 MHz DMSO $d_6$) were in accordance with the expected structure.

Elemental Analysis:

| Theory: | C43.96 | H4.26 | N15.77 | O13.51 | Br22.50 |
| --- | --- | --- | --- | --- | --- |
| Found: | C44.09 | H4.22 | N15.44 | O14.37 | Br21.50 |

Step 3: Synthesis of 3-[5-(benzylamino)-3-bromo-4-nitro-1H-pyrazol-1-yl]propyl methanesulfonate (Compound 3)

0.126 mol of 3-[5-(benzylamino)-3-bromo-4-nitro-1H-pyrazol-1-yl]propan-1-ol (compound 2) and 15.82 mol of triethylamine were introduced, with stirring, into a 500 ml three-necked flask containing 200 ml of THF. The mixture obtained was then cooled to 5° C. and 0.126 mol of mesyl chloride was poured in over 45 minutes.

The reaction medium was maintained at this temperature for 2 hours and the 3-[5-(benzylamino)-3-bromo-4-nitro-1H-pyrazol-1-yl]propyl methanesulfonate (compound 3) was then precipitated by pouring the reaction medium onto 800 ml of ice.

After filtering, the solid was washed thoroughly with water and with diisopropyl ether. Drying was performed under vacuum in the presence of $P_2O_5$. The yield for this step was 94%.

The mass of the expected compound $C_{14}H_{17}BrN_4O_5S$ was detected by mass spectrometry.

The NMR analyses ($^1$H 400 MHz and $^{13}$C 100.61 MHz DMSO $d_6$) were in accordance with the expected structure.

Elemental Analysis:

| Theory: | C38.81 | H3.96 | N12.93 | O18.46 | S7.40 | Br18.44 |
|---|---|---|---|---|---|---|
| Found: | C39.03 | H3.91 | N12.83 | O18.52 | S7.29 | Br18.26 |

Step 4: Synthesis of 3-(benzylamino)-2-nitro-6,7-dihydro-1H,5H-pyrazolo[1,2-a]pyrazol-1-one (Compound 4)

0.1 mol of 3-[5-(benzylamino)-3-bromo-4-nitro-1H-pyrazol-1-yl]propyl methanesulfonate (compound 3) was dispersed in a 500 ml three-necked flask containing 300 ml of pentanol, and the reaction medium was maintained at 130° C. for 2 hours.

After cooling to room temperature, the solid formed was filtered off by suction on a sinter funnel, washed with diisopropyl ether, and dried under vacuum in the presence of $P_2O_5$. The 3-(benzylamino)-2-nitro-6,7-dihydro-1H,5H-pyrazolo[1,2-a]pyrazol-1-one (compound 4) was obtained in a yield of 86%.

The NMR analyses ($^1$H 400 MHz and $^{13}$C 100.61 MHz DMSO $d_6$) were in accordance with the expected structure.

The mass of the expected compound $C_6H_{11}N_4O$ was detected by mass spectrometry.

Elemental Analysis:

| Theory: | C56.72 | H5.49 | N20.36 | O17.44 |
|---|---|---|---|---|
| Found: | C56.68 | H5.13 | N20.38 | O17.69 |

Step 5: Synthesis of 2,3-diamino-6,7-dihydro-1H,5H-pyrazolo[1,2-a]pyrazol-1-one dihydrochloride (Compound 5)

20 g of 3-(benzylamino)-2-nitro-6,7-dihydro-1H,5H-pyrazolo[1,2-a]pyrazol-1-one (compound 4) and 4 g of 5% palladium-on-charcoal were introduced into a 1 liter autoclave containing 800 ml of ethanol. The reduction was then performed under a hydrogen pressure of 8 bar and at a temperature of between 50° C. and 100° C. (with a stirring rate ranging from 1,000 to 2,500 rpm).

After reaction for 4 hours, there was no further consumption of hydrogen and the medium was cooled to 20° C.

The catalyst was removed under nitrogen by filtration, and hydrochloric ethanol was then added to the filtrate. The crystalline product was filtered off by suction, washed with diisopropyl ether, and then dried under vacuum in the presence of $P_2O_5$. The 2,3-diamino-6,7-dihydro-1H,5H-pyrazolo[1,2-a]pyrazol-1-one dihydrochloride (compound 5) was obtained in a yield of 89%.

The mass of the expected compound was detected by mass spectrometry.

The NMR analyses ($^1$H 400 MHz and $^{13}$C 100.61 MHz DMSO $d_6$) were in accordance with the expected structure.

Elemental Analysis:

| Theory: | C31.73 | H5.33 | N24.67 | O7.07 | Cl31.22 |
|---|---|---|---|---|---|
| Found: | C31.45 | H5.20 | N24.62 | O7.24 | Cl30.86 |

Example 2

Synthesis of 2-amino-3-(ethylamino)-6,7-dihydro-1H,5H-pyrazolo[1,2-a]pyrazol-1-one dihydrochloride (Compound 9)

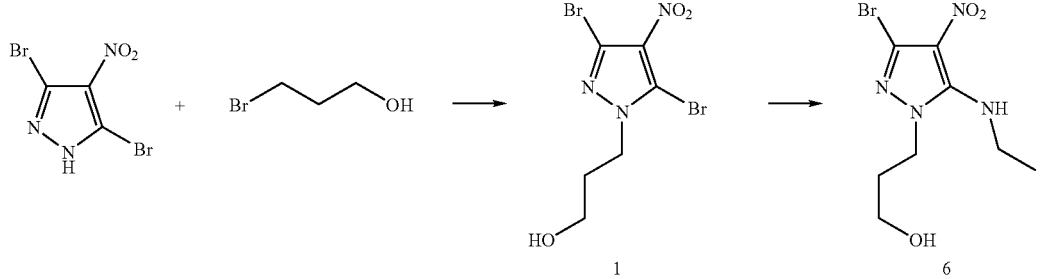

-continued

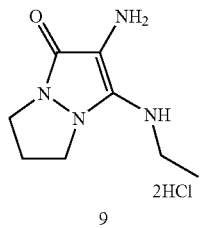

9

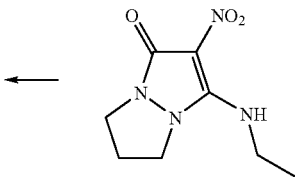

8

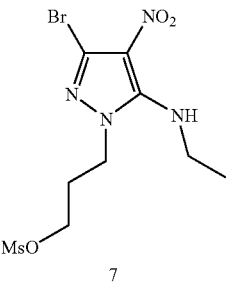

7

Step 1: Synthesis of 3-(3,5-dibromo-4-nitro-1H-pyrazol-1-yl)propan-1-ol (Compound 1)

This step was performed as described above in Example 1.

Step 2: Synthesis of 3-[3-bromo-5-(ethylamino)-4-nitro-1H-pyrazol-1-yl]propan-1-ol (Compound 6)

15 mmol of 3-(3,5-dibromo-4-nitro-1H-pyrazol-1-yl)propan-1-ol were introduced into 30 ml of ethanol in a three-necked flask, with stirring. The homogeneous medium was heated to 75° C. and 93 mmol of ethylamine were then added dropwise and stirring was continued for four hours.

After cooling to room temperature, the medium was poured onto ice and the 3-[3-bromo-5-(ethylamino)-4-nitro-1H-pyrazol-1-yl]propan-1-ol (compound 6) precipitated.

The yellow solid was filtered off by suction and then washed thoroughly with water and diisopropyl ether. Drying was performed under vacuum in the presence of $P_2O_5$. The recovered mass was 3.6 g.

The NMR analyses ($^1H$ 400 MHz and $^{13}C$ 100.61 MHz DMSO $d_6$) were in accordance with the expected structure.

The mass of the expected compound $C_8H_{13}BrN_4O_3$ was detected by mass spectrometry.

Step 3: Synthesis of 3-[5-(ethylamino)-3-bromo-4-nitro-1H-pyrazol-1-yl]propyl methanesulfonate (Compound 7)

11.2 mmol of 3-[3-bromo-5-(ethylamino)-4-nitro-1H-pyrazol-1-yl]propan-1-ol (compound 6) and 1.6 ml of triethylamine were introduced, with stirring, into a 100 ml three-necked flask containing 30 ml of THF. The homogeneous orange mixture obtained was cooled to 0° C. and 1.44 ml of mesyl chloride were added over 20 minutes.

The reaction medium was maintained at this temperature for 2 hours and the 3-[5-(ethylamino)-3-bromo-4-nitro-1H-pyrazol-1-yl]propyl methanesulfonate (compound 7) was precipitated by pouring the reaction medium onto 500 ml of ice.

The yellow solid was filtered by suction and then washed thoroughly with water and diisopropyl ether; drying was performed under vacuum in the presence of $P_2O_5$. The recovered mass was 3.1 g.

The NMR analyses ($^1H$ 400 MHz and $^{13}C$ 100.61 MHz DMSO $d_6$) were in accordance with the expected structure.

The mass of the expected compound $C_9H_{15}BrN_4O_5S$ was detected by mass spectrometry.

Step 4: Synthesis of 3-(ethylamino)-2-nitro-6,7-dihydro-1H,5H-pyrazolo[1,2-a]pyrazol-1-one (Compound 8)

8 mmol of 3-[5-(ethylamino)-3-bromo-4-nitro-1H-pyrazol-1-yl]propyl methanesulfonate (compound 7) were dispersed, with stirring, in a 50 ml three-necked flask containing 20 ml of pentanol, and the reaction medium was maintained at 130° C. for 2 hours.

After cooling to room temperature, the solid formed was filtered off by suction and then washed with diisopropyl ether.

After drying under vacuum in the presence of $P_2O_5$, 1.46 g of 3-(ethylamino)-2-nitro-6,7-dihydro-1H,5H-pyrazolo[1,2-a]pyrazol-1-one (compound 8) were obtained.

The NMR analyses ($^1H$ 400 MHz and $^{13}C$ 100.61 MHz DMSO $d_6$) were in accordance with the expected structure.

The mass of the expected compound was detected by mass spectrometry.

Step 5: Synthesis of 2-amino-3-(ethylamino)-6,7-dihydro-1H,5H-pyrazolo[1,2-a]pyrazol-1-one dihydrochloride (Compound 9)

1.45 g of 3-(ethylamino)-2-nitro-6,7-dihydro-1H,5H-pyrazolo[1,2-a]pyrazol-1-one (compound 8) and 300 mg of 5% palladium-on-charcoal were introduced into a 300 ml autoclave containing 200 ml of ethanol. The reduction was performed at a hydrogen pressure of 8 bar at a temperature of 60° C. (stirring at 1700 rpm).

After reaction for 2 hours, there was no further consumption of hydrogen and the reaction medium was cooled to 20° C.

The catalyst was removed by filtration under nitrogen and the filtrate was diluted with 100 ml of hydrochloric isopropyl ether.

The pale yellow solution was evaporated to dryness and the solid was then taken up in an ethanol/isopropyl ether mixture. The 2-amino-3-(ethylamino)-6,7-dihydro-1H,5H-pyrazolo[1,2-a]pyrazol-1-one hydrochloride (compound 9) precipitated; it was filtered off by suction and, after drying under vacuum in the presence of $P_2O_5$, 1.18 g of 2-amino-3-(ethylamino)-6,7-dihydro-1H,5H-pyrazolo[1,2-a]pyrazol-1-one dihydrochloride (compound 9) were recovered.

The NMR analyses ($^1H$ 400 MHz and $^{13}C$ 100.61 MHz DMSO $d_6$) were in accordance with the expected structure.

The mass of the expected compound $C_8H_{14}N_4O$ was detected by mass spectrometry.

Example 3

Synthesis of 2-amino-3-(isopropylamino)-6,7-dihydro-1H,5H-pyrazolo[1,2-a]pyrazol-1-one (Compound 13)

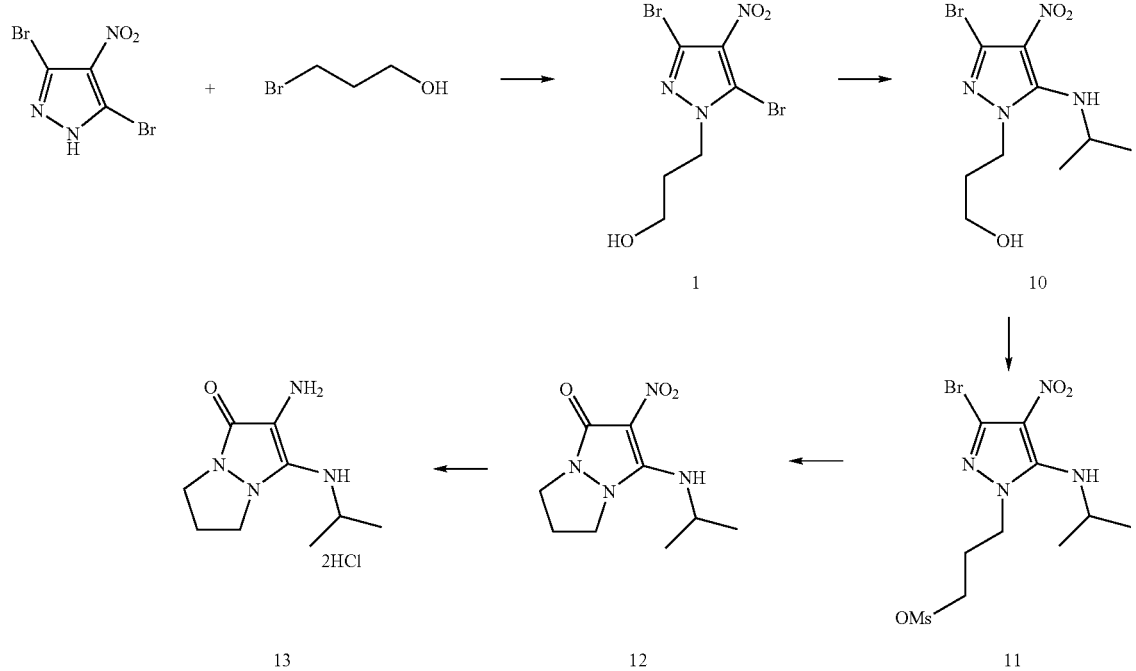

Step 1: Synthesis of 3-(3,5-dibromo-4-nitro-1H-pyrazol-1-yl)propan-1-ol (Compound 1)

This step was performed as described above in Example 1.

Step 2: Synthesis of 3-[3-bromo-5-(isopropylamino)-4-nitro-1H-pyrazol-1-yl]propan-1-ol (Compound 10)

15 mmol of 3-(3,5-dibromo-4-nitro-1H-pyrazol-1-yl)propan-1-ol were introduced, with stirring, into 30 ml of ethanol in a three-necked flask. The homogeneous medium was heated to 75° C. and 93 mmol of isopropylamine were then added dropwise with continued stirring for 4 hours.

After cooling to room temperature, the medium was poured onto ice and then neutralized with hydrochloric acid. The 3-[3-bromo-5-(isopropylamino)-4-nitro-1H-pyrazol-1-yl]propan-1-ol (compound 10) was extracted with dichloromethane.

After drying the organic phase over sodium sulfate and removing the solvent by evaporation under vacuum, 4.37 g of 3-[3-bromo-5-(isopropylamino)-4-nitro-1H-pyrazol-1-yl]propan-1-ol (compound 10) were obtained.

The NMR analyses ($^1$H 400 MHz and $^{13}$C 100.61 MHz DMSO $d_6$) were in accordance with the expected structure.

The mass of the expected compound $C_9H_{15}BrN_4O_3$ was detected by mass spectrometry.

Step 3: Synthesis of 3-[5-(isopropylamino)-3-bromo-4-nitro-1H-pyrazol-1-yl]propyl methanesulfonate 11

13.7 mmol of 3-[3-bromo-5-(isopropylamino)-4-nitro-1H-pyrazol-1-yl]propan-1-ol (compound 10) and 1.94 ml of triethylamine were introduced, with stirring, into a 50 ml three-necked flask containing 20 ml of THF. The homogeneous orange mixture thus obtained was cooled to 0° C. and 1.76 ml of mesyl chloride were added over 20 minutes.

The reaction medium was maintained at this temperature for 2 hours, and 3-[5-(ethylamino)-3-bromo-4-nitro-1H-pyrazol-1-yl]propyl methanesulfonate (compound 11) was then precipitated by pouring the reaction medium onto 500 ml of ice.

The yellow solid was filtered off by suction and then washed thoroughly with water and petroleum ether, and was dried under vacuum in the presence of $P_2O_5$. The recovered mass was 4.2 g.

The NMR analyses ($^1$H 400 MHz and $^{13}$C 100.61 MHz DMSO $d_6$) were in accordance with the expected structure.

The mass of the expected compound was detected by mass spectrometry.

Step 4: Synthesis of 3-(isopropylamino)-2-nitro-6,7-dihydro-1H,5H-pyrazolo[1,2-a]pyrazol-1-one (Compound 12)

10 mmol of 3-[5-(isopropylamino)-3-bromo-4-nitro-1H-pyrazol-1-yl]propyl methanesulfonate (compound 11) were dispersed, with stirring, in 20 ml of pentanol in a 50 ml three-necked flask, and the mixture was heated at 130° C. for 2 hours.

After cooling to room temperature, the solid obtained was filtered off by suction on a sinter funnel and washed with diisopropyl ether.

After drying under vacuum in the presence of $P_2O_5$, 1.71 g of 3-(isopropylamino)-2-nitro-6,7-dihydro-1H,5H-pyrazolo[1,2-a]pyrazol-1-one (compound 12) were obtained.

The NMR analyses ($^1$H 400 MHz and $^{13}$C 100.61 MHz DMSO $d_6$) were in accordance with the expected structure.

The mass of the expected compound $C_9H_{14}N_4O_3$ was detected by mass spectrometry.

The NMR analyses ($^1$H 400 MHz and $^{13}$C 100.61 MHz DMSO $d_6$) were in accordance with the expected structure.

The mass of the expected compound $C_9H_{16}N_4O$ was detected by mass spectrometry.

Example 4

2-Amino-3-(pyrrolidin-1-yl)-6,7-dihydro-1H,5H-pyrazolo[1,2-a]pyrazol-1-one dihydrochloride (Compound 17)

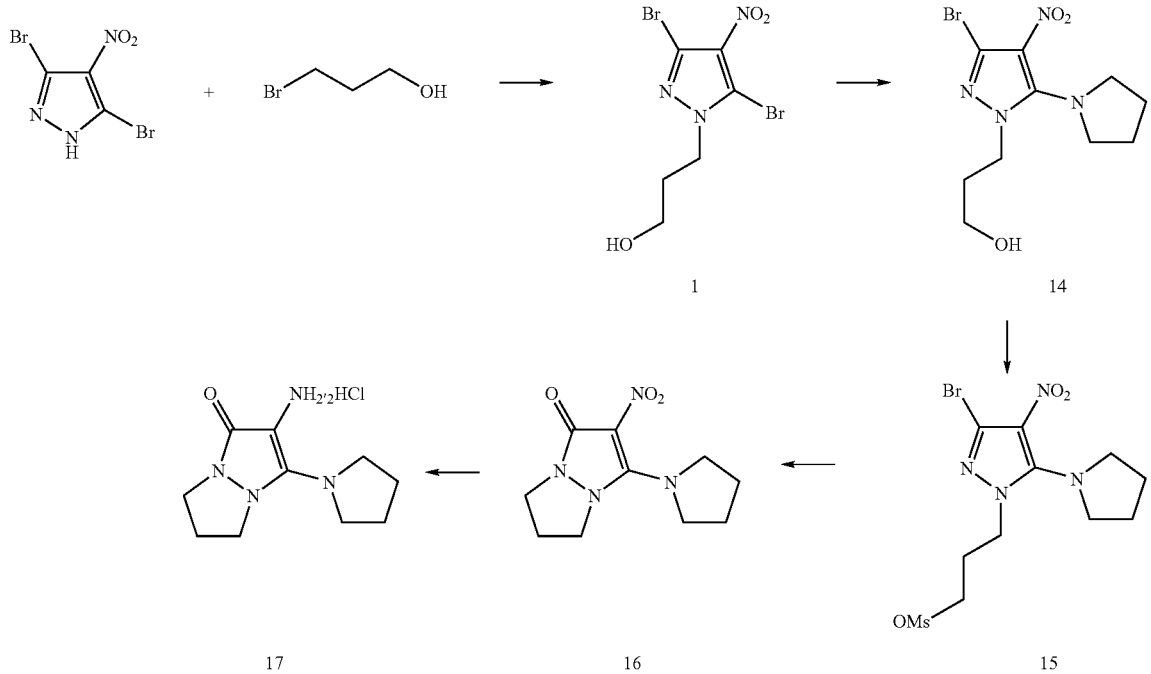

Step 5: Synthesis of 2-amino-3-(isopropylamino)-6,7-dihydro-1H,5H-pyrazolo[1,2-a]pyrazol-1-one dihydrochloride (Compound 13)

1.70 g of 3-(isopropylaminoamino)-2-nitro-6,7-dihydro-1H,5H-pyrazolo[1,2-a]pyrazol-1-one (compound 12) and 300 mg of 5% palladium-on-charcoal were introduced into a 300 ml autoclave containing 200 ml of ethanol. The reaction was performed at a temperature of 60° C. and at a hydrogen pressure of 6 bar (stirring at 2,000 rpm).

After reaction for 2 hours, there was no further consumption of hydrogen, and the medium was cooled to 20° C.

The catalyst was removed by filtration under nitrogen after cooling to room temperature, and hydrochloric isopropyl ether was added.

The pale yellow solution was evaporated to dryness and the solid was then taken up in 50 ml of diisopropyl ether saturated with hydrogen chloride, and the precipitate was recovered by suction filtration. After drying under vacuum in the presence of $P_2O_5$, 1.5 g of 2-amino-3-(isopropylamino)-6,7-dihydro-1H,5H-pyrazolo[1,2-a]pyrazol-1-one dihydrochloride (compound 13) were isolated.

Step 1: Synthesis of 3-(3,5-dibromo-4-nitro-1H-pyrazol-1-yl)propan-1-ol (Compound 1)

This step was performed as described above in Example 1.

Step 2: 3-(3-Bromo-4-nitro-5-(pyrrolidin-1-yl)-1H-pyrazol-1-yl)propan-1-ol (Compound 14)

15 mmol of 3-(3,5-dibromo-4-nitro-1H-pyrazol-1-yl)propan-1-ol were introduced, with stirring, into 20 ml of isopropanol in a three-necked flask. The homogeneous medium was heated to 75° C. and 90 mmol of pyrrolidine were then added dropwise and stirring was continued for 2 hours.

After cooling to room temperature, the medium was poured onto ice and neutralized with hydrochloric acid. The 3-(3-bromo-4-nitro-5-(pyrrolidin-1-yl)-1H-pyrazol-1-yl)propan-1-ol (compound 14) was extracted with dichloromethane.

After drying the organic phase over sodium sulfate and distilling off the solvent by evaporation under vacuum, 4.8 g of 3-(3-bromo-4-nitro-5-(pyrrolidin-1-yl)-1H-pyrazol-1-yl)propan-1-ol (compound 14) were obtained.

The NMR analyses ($^1$H 400 MHz and $^{13}$C 100.61 MHz DMSO $d_6$) were in accordance with the expected structure.

The mass of the expected compound $C_{10}H_{17}BrN_4O$ was detected by mass spectrometry.

Step 3: Synthesis of 3-(3-bromo-4-nitro-5-(pyrrolidin-1-yl)-1H-pyrazol-1-yl)propyl methanesulfonate (Compound 15)

30 mmol of 3-(3-bromo-4-nitro-5-(pyrrolidin-1-yl)-1H-pyrazol-1-yl)propan-1-ol (compound 14) and 4.25 ml of triethylamine were introduced, with stirring, into a 100 ml three-necked flask containing 50 ml of THF. The homogeneous orange mixture obtained was cooled to 0° C. and 2.32 ml of mesyl chloride were added over 20 minutes.

The reaction medium was maintained at this temperature for 2 hours and the 3-(3-bromo-4-nitro-5-(pyrrolidin-1-yl)-1H-pyrazol-1-yl)propyl methanesulfonate (compound 15) was then precipitated by pouring the reaction medium onto ice.

The solid was filtered off by suction and then dried under vacuum in the presence of $P_2O_5$. The recovered mass was 9.3 g.

The NMR analyses ($^1$H 400 MHz and $^{13}$C 100.61 MHz DMSO $d_6$) were in accordance with the expected structure.

The mass of the expected compound $C_{11}H_{19}BrN_4O_3S$ was detected by mass spectrometry.

Step 4: Synthesis of 2-nitro-3-(pyrrolidin-1-yl)-6,7-dihydro-1H,5H-pyrazolo[1,2-a]pyrazol-1-one (Compound 16)

22.5 mmol of 3-(3-bromo-4-nitro-5-(pyrrolidin-1-yl)-1H-pyrazol-1-yl)propyl methanesulfonate (compound 15) were introduced into 100 ml of pentanol, with stirring, in a 250 ml three-necked flask. The medium thus obtained was maintained at 130° C. for 2 hours.

After cooling to room temperature, the 2-nitro-3-(pyrrolidin-1-yl)-6,7-dihydro-1H,5H-pyrazolo[1,2-a]pyrazol-1-one (compound 16) was extracted with dichloromethane.

After drying the organic phase over sodium sulfate and distilling off the solvent under vacuum, 1.2 g of 2-nitro-3-pyrrolidin-1-yl-6,7-dihydro-1H,5H-pyrazolo[1,2-a]pyrazol-1-one (compound 16) were obtained.

The NMR analyses ($^1$H 400 MHz and $^{13}$C 100.61 MHz DMSO $d_6$) were in accordance with the expected structure.

The mass of the expected compound $C_{10}H_{14}N_4O_3$ was detected by mass spectrometry.

Step 5: Synthesis of 2-amino-3-(pyrrolidin-1-yl)-6,7-dihydro-1H,5H-pyrazolo[1,2-a]pyrazol-1-one dihydrochloride (Compound 17)

1.1 g of 2-nitro-3-(pyrrolidin-1-yl)-6,7-dihydro-1H,5H-pyrazolo[1,2-a]pyrazol-1-one (compound 16) and 300 mg of 5% palladium-on-charcoal were introduced into a 300 ml autoclave containing 200 ml of ethanol. The reduction was performed with stirring at 2,000 rpm, at a temperature of 60° C. and under a hydrogen pressure of 6 bar.

After reaction for 2 hours, there was no further consumption of hydrogen, and the medium was cooled to 20° C.

The catalyst was removed by filtration under nitrogen after cooling to room temperature, and hydrochloric isopropyl ether was added.

The pale yellow solution was evaporated to dryness and the solid was then taken up in 50 ml of diisopropyl ether saturated with hydrogen chloride, and the precipitate was recovered by suction filtration. After drying under vacuum in the presence of $P_2O_5$, 1.5 g of 2-amino-3-(pyrrolidin-1-yl)-6,7-dihydro-1H,5H-pyrazolo[1,2-a]pyrazol-1-one dihydrochloride (compound 17) were obtained.

The NMR analyses ($^1$H 400 MHz and $^{13}$C 100.61 MHz DMSO $d_6$) were in accordance with the expected structure.

The mass of the expected compound $C_{10}H_{16}N_4O$ was detected by mass spectrometry.

Example 5

Synthesis of 2,3-diamino-6,7-dihydro-1H,5H-pyrazolo[1,2-a]pyrazol-1-one dimethanesulfonate (Compound 3)

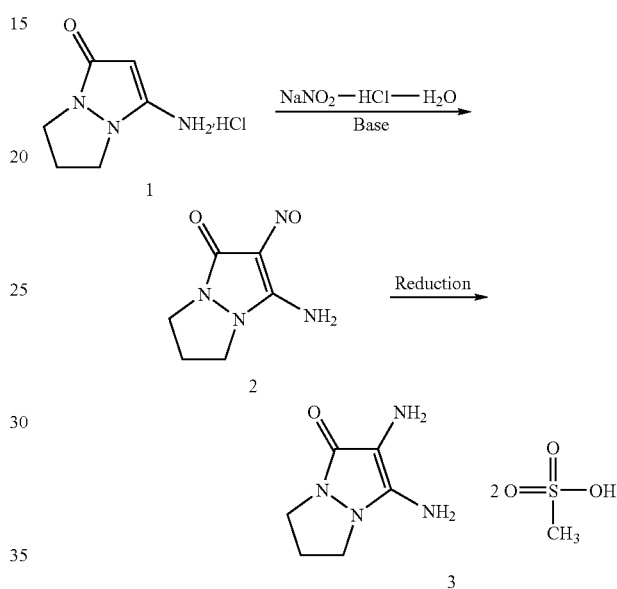

Step 1: Synthesis of 3-amino-2-nitroso-6,7-dihydro-1H,5H-pyrazolo[1,2-a]pyrazol-1-one (Compound 2)

43 g (0.245 mol) of 3-amino-6,7-dihydro-1H,5H-pyrazolo[1,2-a]pyrazol-1-one hydrochloride were dissolved, with stirring, at room temperature, in a mixture of 180 ml of water and 35 ml of 35% hydrochloric acid in a 500 ml three-necked flask.

The mixture was cooled to 0° C. and a solution of 17.3 g of sodium nitrite (0.25 mol) in 20 ml of water was added dropwise over 30 minutes. The temperature of the reaction medium was maintained between 0 and +5° C. throughout the addition and for one hour after the end of the addition.

The reaction medium was brought to pH 8 by adding sodium hydroxide, with stirring, while maintaining the temperature in a range of from 0 to 5° C. The 3-amino-2-nitroso-6,7-dihydro-1H,5H-pyrazolo[1,2-a]pyrazol-1-one (compound 2) precipitated in the form of a red-orange solid, which was filtered off on a No. 4 sinter funnel, slurried in a minimum amount of 2-propanol, washed with diisopropyl ether, and dried under vacuum in the presence of phosphorus pentoxide. 35 g of orange-red product were thus obtained (yield: 85%).

The NMR ($^1$H 400 MHz and $^{13}$C 100.61 MHz DMSO $d_6$) and mass spectra were in accordance with the expected structure 2.

Step 2: Synthesis of 2,3-diamino-6,7-dihydro-1H, 5H-pyrazolo[1,2-a]pyrazol-1-one dimethanesulfonate (Compound 3)

33.6 g (0.2 mol) of 3-amino-2-nitroso-6,7-dihydro-1H,5H-pyrazolo[1,2-a]pyrazol-1-one (compound 2), 500 ml of ethanol and 6 g of 5% palladium-on-charcoal containing 50% water were introduced into a 1 liter autoclave.

The medium was flushed 3 times with nitrogen and then 3 times with hydrogen and the temperature of the mixture was brought to 40° C.

The reduction was performed over two hours at a pressure of 8 bar. This reduction was exothermic and the temperature spontaneously rose to 70° C.

The temperature was allowed to fall to 50° C. and the catalyst was then filtered off on a filterpress under a stream of nitrogen.

The filtrate was poured into a mixture of 50 ml of ethanol and 40 ml of methanesulfonic acid, with cooling to 0° C. The 2,3-diamino-6,7-dihydro-1H,5H-pyrazolo-[1,2-a]pyrazol-1-one dimethanesulfonate (compound 3) crystallized in the form of a pale yellow solid, which was filtered off by suction on a No.4 sinter funnel, washed with diisopropyl ether and then with petroleum ether and finally dried under vacuum in the presence of phosphorus pentoxide. 43 g of pale yellow solid were thus obtained (yield: 65%).

The NMR ($^1$H 400 MHz and $^{13}$C 100.61 MHz DMSO $d_6$) and mass spectra were in accordance with the expected structure 3.

Elemental Analysis:

| Theory: | C27.74 | H5.23 | N16.17 | O32.33 | S18.51 |
|---|---|---|---|---|---|
| Found: | C27.16 | H5.22 | N15.63 | O32.81 | S18.64 |

Example 6

Synthesis of 2,3-diamino-5,6,7,8-tetrahydro-1H-pyrazolo[1,2-a]pyridazin-1-one hydrochloride (Compound E)

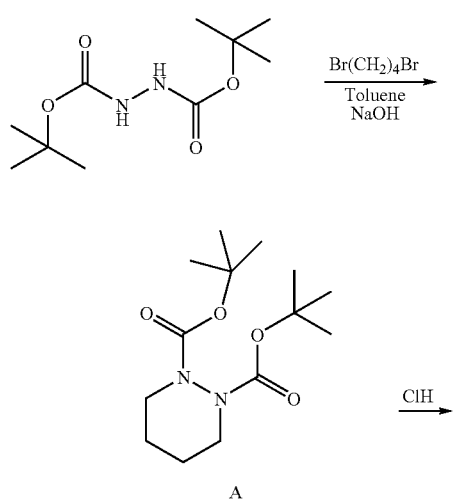

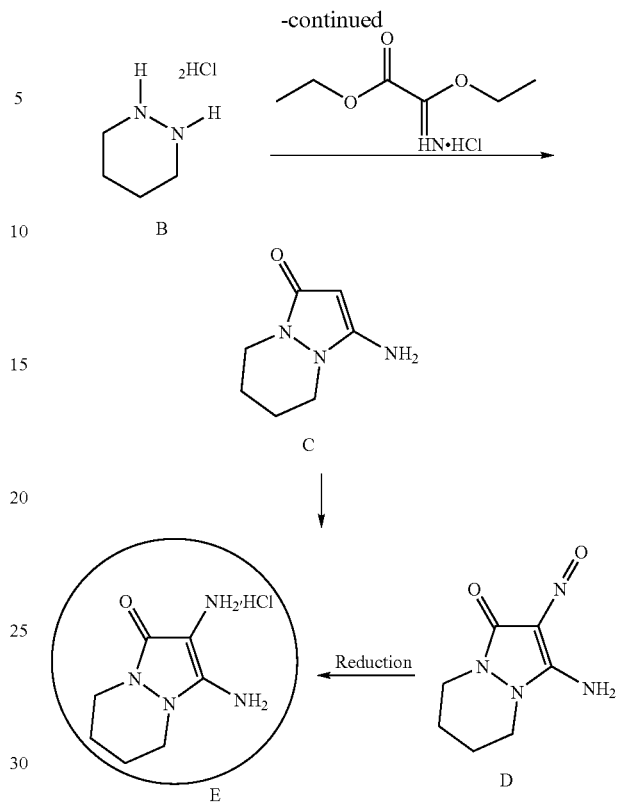

Step 1: Synthesis of di-tert-butyl tetrahydropyridazine-1,2-dicarboxylate (Compound A)

50 ml of toluene, 5 g (21.5 mmol) of N,N'-di-tert-butoxycarbonyl hydrazide, 680 mg of tetraethylammonium bromide and 25 ml of 50% sodium hydroxide were introduced, with mechanical stirring, into a 250 ml three-necked flask equipped with a condenser, a thermometer, and a dropping funnel.

The heterogeneous medium was heated to 100° C. and 1,4-dibromobutane was then added dropwise over 15 minutes.

The reaction medium was heated at 100° C. for 3 days. After cooling, 100 ml of ethyl acetate were added and the mixture was transferred into a separating funnel. The organic phase was washed with 4×70 ml of saturated aqueous sodium carbonate solution and then with 4×70 ml of water, and finally with 4×70 ml of brine. The organic phase was dried over sodium sulfate and the solvent was evaporated off under vacuum. A colorless oil that crystallize as a white solid was thus obtained. A mass of 6.1 g was recovered (yield: 99%).

The NMR ($^1$H 400 MHz and $^{13}$C 100.61 MHz DMSO $d_6$) and mass spectra were in accordance with the expected structure A.

Step 2: Synthesis of hexahydropyridazine dihydrochloride (Compound B)

5.9 g of compound A were introduced into 50 ml of a 3/1 mixture of dioxane and 35% hydrochloric acid, with mechanical stirring, in a 100 ml three-necked flask equipped with a condenser and a thermometer.

The colorless solution obtained was stirred at room temperature for 3 hours and the reaction medium was then diluted with diisopropyl ether. The solvents were evaporated off under vacuum. The pasty residue obtained was taken up in an ether/ethanol mixture. After filtering off the solid and drying under vacuum, 1.39 g of white solid were obtained.

The NMR ($^1$H 400 MHz and $^{13}$C 100.61 MHz DMSO $d_6$) and mass spectra were in accordance with the expected structure B.

Step 3: Synthesis of 3-amino-5,6,7,8-tetrahydro-1H-pyrazolo[1,2-a]pyridazin-1-one: (Compound C)

7.5 ml of ethanol, 1.5 ml of triethylamine and 0.73 ml of 3-amino-3-ethoxyacrylic acid were introduced, with mechanical stirring, into a 25 ml three-necked flask equipped with a condenser and a thermometer. 500 mg of hexahydropyridazine dihydrochloride (compound B) were then added and the mixture was stirred for 3 hours at room temperature.

The insoluble material was filtered off and the solvent was distilled off under vacuum. The solid was taken up in a minimum amount of water, filtered off, and dried under vacuum. 0.9 g of a slightly yellow powder was thus obtained.

The NMR ($^1$H 400 MHz and $^{13}$C 100.61 MHz DMSO $d_6$) and mass spectra were in accordance with the expected structure C.

Step 4: Synthesis of 3-amino-2-nitroso-5,6,7,8-tetrahydro-1H-pyrazolo[1,2-a]pyridazin-1-one: (Compound D)

20 ml of 35% hydrochloric acid and 1 g of 3-amino-5,6,7,8-tetrahydro-1H-pyrazolo[1,2-a]pyridazin-1-one (compound C) were introduced, with mechanical stirring, into a 50 ml three-necked flask equipped with a condenser and a thermometer.

The mixture was cooled to 0° C. and a solution of 675 mg of sodium nitrite in 5 ml of water was added, while maintaining this temperature. The color of the reaction mixture changed from yellow to orange and a precipitate began to form.

After 30 minutes the reaction was complete, and the orange solid was filtered off on a No. 4 sinter funnel, washed with water, and then dried under vacuum. The yield was 78.3%.

The NMR ($^1$H 400 MHz and $^{13}$C 100.61 MHz DMSO $d_6$) and mass spectra were in accordance with the expected structure D.

Step 5: Synthesis of 2,3-diamino-5,6,7,8-tetrahydro-1H-pyrazolo[1,2-a]pyridazin-1-one hydrochloride: (Compound E)

1.3 g of 3-amino-2-nitroso-5,6,7,8-tetrahydro-1H-pyrazolo[1,2-a]pyridazin-1-one (compound D) and 250 mg of 5% palladium-on-charcoal were introduced into a 300 ml autoclave containing 250 ml of ethanol. The reduction was performed with stirring at 2,000 rpm, at a temperature of 60° C. and under a hydrogen pressure of 6 bar.

After reaction for 2 hours, there was no further consumption of hydrogen, and the medium was cooled to 20° C.

The catalyst was removed by filtration under nitrogen after cooling to room temperature, and the solution was poured into 75 ml of hydrochloric dioxane.

The solution thus obtained was evaporated until a slightly yellow powder was obtained, which was taken up in diisopropyl ether.

The solid was recovered by filtration. After drying under vacuum in the presence of phosphorus pentoxide, 1.1 g of 2,3-diamino-5,6,7,8-tetrahydro-1H-pyrazolo-[1,2-a]pyridazin-1-one dihydrochloride were obtained.

The NMR ($^1$H 400 MHz and $^{13}$C 100.61 MHz DMSO $d_6$) and mass spectra were in accordance with the expected structure E.

Example 7

Synthesis of 4-amino-1,2-diethyl-5-pyrrolidin-1-yl-1,2-dihydropyrazol-3-one hydrochloride

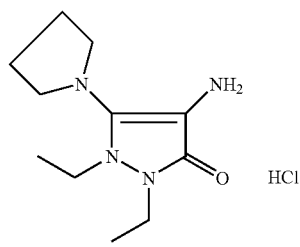

Step 1: Synthesis of 1,2-diethylpyrazolidine-3,5-dione 100 g of diethylhydrazine dihydrochloride (0.63 mol) in 1,000 ml of dichloromethane, 85.3 g of malonic acid (0.82 mol; 1.3 eq.), 196 g of hydroxybenzotriazole (1.45 mol; 2.3 eq.), and 278 g of 1-(3-dimethylaminopropyl)-3-ethylcarbodiimide hydrochloride (EDCI; 1.45 mol: 2.3 eq.) were successively introduced, with magnetic stirring, into a 3,000 ml three-necked flask under a nitrogen atmosphere, equipped with a thermometer.

The reaction medium was then cooled to a tempurature ranging from 0° C. to 5° C. 407 g of N,N-diisopropylethylamine (3.14 mol; 520 ml: 5 eq.) were then added slowly thereto. At the end of the addition, the reaction medium, which has become homogeneous, was stirred at room temperature. After leaving overnight at room temperature, the reaction was complete.

The reaction medium was washed with 3×600 ml of deionized water. The organic phase was dried over sodium sulfate, filtered, and concentrated under vacuum to give 46 g of crude product. Since the pyrazolidinedione is soluble in aqueous medium, the aqueous phase was thus concentrated to dryness and then taken up in 800 ml of 1 N hydrochloric acid solution. The precipitate formed was filtered off and the aqueous phase was extracted with 3×1300 ml of dichloromethane. The combined organic phases were dried over sodium sulfate, filtered, and concentrated under vacuum to give 67.5 g of crude product.

1,2-Diethylpyrazolidine-3,5-dione was thus obtained in the form of a yellow solid in a yield of 40% (39.5 g).

Step 2: Synthesis of 1,2-diethyl-3-chloro-5-pyrazolone 30 g of 1,2-diethylpyrazolidine-3,5-dione (0.19 mol) dissolved in 200 ml of toluene and 35.8 ml of trichlorophosphine oxide (258.9 g; 0.38 mol; 2 eq.) were introduced, under a nitrogen atmosphere, into a 500 ml three-necked flask equipped with a condenser and a magnetic stirrer.

The reaction medium was brought to the reflux temperature of the toluene and the reaction was monitored by TLC (95/5 dichloromethane/methanol). The reaction medium, which was initially in the form of a paste, homogenized as soon as the refluxing started and then became a two-phase mixture.

After refluxing for one hour, the reaction was hydrolysed at 0° C. by very slow addition of 100 ml of deionized water. After settling of the phases, the toluene phase was separated from the aqueous phase. The aqueous phase was washed with 50 ml of toluene and then brought to pH 12 with 184 ml of 35% sodium hydroxide solution. The formation of a precipitate was observed. The aqueous phase was maintained at 100° C. for 10 minutes and the precipitate dissolved. The reaction medium was then in two phases. The brown-colored upper phase was separated out after settling of the phases while hot. This upper phase was dissolved in 200 ml of dichloromethane, washed once with 50 ml of deionized water, dried over sodium sulfate, and concentrated under vacuum to give 20.5 g of a brown oil.

A precipitate formed in the lower aqueous phase on cooling to room temperature. After filtering off through a sinter funnel, the precipitate was rinsed with water and the filtrate was extracted with 3×300 ml of dichloromethane. The dichloromethane phase was dried over sodium sulfate and concentrated under vacuum to give 5.5 g of brown crystals.

The oil and the brown crystals were collected, grafted on silica, and chromatographed on silica gel (40-60 μm; 2000 g) with an elution gradient:
1) 100 dichloromethane (13 liters)
2) 99.5/0.5 dichloromethane/MeOH (0.8 liter)
3) 99/1 dichloromethane/MeOH (8 liters) expected product+ 15% impurity m=6.6 g
4) 98.5/1.5 dichloromethane/MeOH (35 liters) expected product (14.7 g).

1,2-Diethyl-3-chloro-5-pyrazolone was thus obtained in the form of yellow crystals in a yield of 44%.

Step 3: Synthesis of 1,2-diethyl-5-pyrrolidin-1-yl-1, 2-dihydropyrazol-3-one

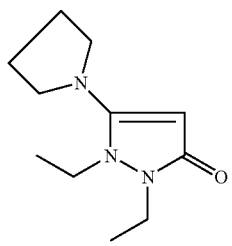

1 g of 5-chloro-1,2-diethyl-1,2-dihydropyrazol-3-one (5.7×10$^{-4}$ mol) was introduced into a 2.5 ml reactor of the Biotage microwave initiator, and 2 ml of pyrrolidine (4.2 eq.) were added thereto.

Operating conditions: microwave at maximum power θ=120° C. for 17 minutes.

After 17 minutes, the reaction was complete (monitoring by TLC, eluent: 90/10 CH$_2$Cl$_2$/MeOH).

5 ml of demineralized water were then added to the reaction medium, and the assembly was then transferred into a separating funnel. The aqueous phase was extracted with 4×10 ml of dichloromethane. The organic phases were then combined and dried over anhydrous sodium sulfate, and then filtered and evaporated to dryness. 1.2 grams of a brown-orange oil were obtained in a yield of 100%.

NMR ($^1$H 400 MHz DMSO d$_6$) Analysis:
0.81 (1t, 3H), 0.89 (1t, 3H), 1.88 (1m, 1H), 3.22 (1m, 4H), 3.4 (1m, 4H), 4.4 (1s, 1H)

Mass analysis was performed by OpenLynx (FIA/MS). The mass mainly detected was in accordance with the expected structure: M=20.

Step 4: Synthesis of 1,2-diethyl-4-nitroso-5-pyrrolidin-1-yl-1,2-dihydro-3H-pyrazol-3-one

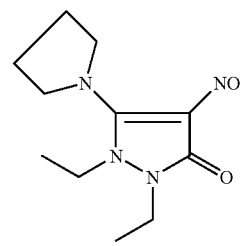

1.2 g of 1,2-diethyl-5-pyrrolidin-1-yl-1,2-dihydropyrazol-3-one were introduced into a fully equipped 25 ml three-necked flask and dissolved in a mixture composed of 0.84 ml of 37% hydrochloric acid and 4 ml of demineralized water.

The reaction medium was cooled to between 0° C. and 5° C. using a bath of ice-water.

A solution composed of 400 mg of sodium nitrite (5.7× 10$^{-4}$ mol) dissolved in 0.6 ml of demineralized water was then added dropwise.

The reaction medium immediately turned bright red as soon as the first drop of the above mixture was added.

After one hour, the reaction was complete.

The pH was adjusted to about 7-8 with 30% sodium hydroxide solution and the reaction medium was then transferred into a separating funnel. The aqueous phase was extracted with 4 times 10 ml of dichloromethane. The organic phases were combined and dried over anhydrous sodium sulfate and then evaporated to dryness. 1.2 grams of a turquoise-blue powder were obtained in a yield of 89.6%.

The NMR ($^1$H 400 MHz DMSO d$_6$) and mass spectra were in accordance with the expected structure.

NMR ($^1$H 400 MHz DMSO d$_6$) Analysis:
0.94 (1t, 3H), 1 (1t, 3H), 2.05 (1m, 4H), 3.51 (1q, 4H), 3.76 (1q, 4H), 3.94 (1m, 4H)

Mass analysis was performed by OpenLynx (FIA/MS). The mass mainly detected was in accordance with the expected structure. M=238.

Step 5: Synthesis of 4-amino-1,2-diethyl-5-pyrrolidin-1-yl-1,2-dihydropyrazol-3-one hydrochloride 4 grams of zinc powder (0.06 mol) were introduced into 300 ml of absolute ethanol in a fully equipped 500 ml three-necked flask, and 1 ml of acetic acid was added thereto.

The reaction medium was heated to 40° C. and 1.15 g (4.8×10⁻³ mol) of 1,2-diethyl-4-nitroso-5-pyrrolidin-1-yl-1,2-dihydro-3H-pyrazol-3-one were then introduced in spatula portions. 4 ml of acetic acid were finally introduced milliliter by milliliter and the medium was brought to reflux. The medium was fully soluble and colorless. After 30 minutes, the reaction was complete on TLC according to the eluent 90/10 ethyl acetate/MeOH.

The reaction medium was cooled and then filtered on a sinter funnel containing a bed of Celite 545. The mother liquors were filtered into a round-bottomed flask containing 2.5 ml of cooled 5N hydrochloric isopropanol. The mixture was then evaporated to dryness. The product obtained was a pink powder that was in accordance by NMR and Mass.

NMR ($^1$H 400 MHz DMSO $d_6$) Analysis:
0.79 (1t, 3H), 0.96 (1t, 3H), 1.87 (1m, 4H), 3.49 (1q, 2H), 3.59 (1m, 6H)

FIA/MS analysis was performed via OpenLynx. The quasi-molecular ions $[M+H]^+$, $[M+Na]^+$, $[2M+H]^+$, and $[2M+Na]^+$ of the expected base $C_{11}H_{20}N_4O$ were mainly detected.

By repeating the above steps with the appropriate reagents, 4-amino-5-[3-(dimethylamino)pyrrolidin-1-yl]-1,2-diethyl-1,2-dihydro-3H-pyrazol-3-one hydrochloride can be obtained.

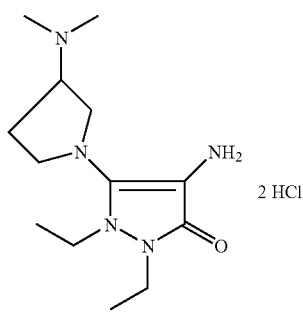

2 HCl

Example 8

Synthesis of the Dye Comprising Two Chromophores Having the Following Formula

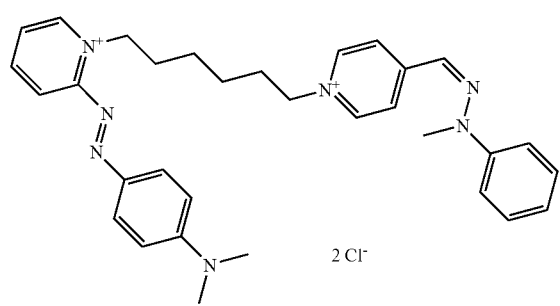

2 Cl⁻

Reaction Scheme:

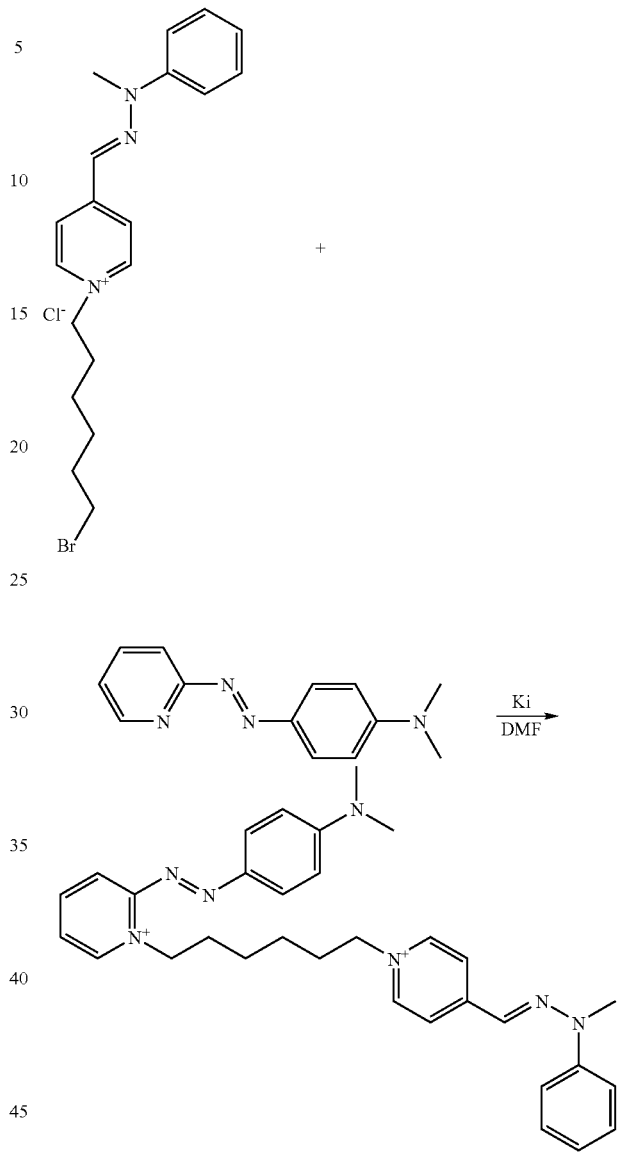

Process:

1.06 equivalents of the hydrazone dye (3 g) and about 100 mg of KI were introduced into 2 ml of DMF, with stirring, and were heated to 95° C.

1 equivalent of the azo dye (1.49 g) dissolved in 5 ml of DMF was then added and the mixture was reacted for 24 hours.

The product was recovered by precipitation from ethyl acetate (50 ml); the product was filtered off and dried, and was in the form of a black powder.

The product was purified by dissolution in dichloromethane followed by precipitation in a mixture containing an isopropanol/ethyl acetate mixture (1/4), and was then filtered off.

The $^{13}$C and $^1$H NMR spectra were in accordance with the structure of the expected product.

DYEING EXAMPLES

Example 1

Compositions A, B, and C were prepared by combining the following components:

|  | Composition A (invention) | Composition B (comparative) | Composition C (comparative) |
|---|---|---|---|
| 2,3-Diamino-6,7-dihydro-1H,5H-pyrazolo[1,2-a]pyrazol-1-one, 2 HCl | $1 \times 10^{-3}$ mol | $1.5 \times 10^{-3}$ mol | — |
| 5,6-Dihydroxyindoline, HBr | $1 \times 10^{-3}$ mol | $1.5 \times 10^{-3}$ mol | — |
| Heterocyclic direct dye of formula (XV)[†] | $1 \times 10^{-3}$ mol | — | $3 \times 10^{-3}$ mol |
| Common dye support No. 1 | () | () | (**) |
| Demineralized water qs | 100 g | 100 g | 100 g |

[†]Heterocyclic direct dye of formula (XV):

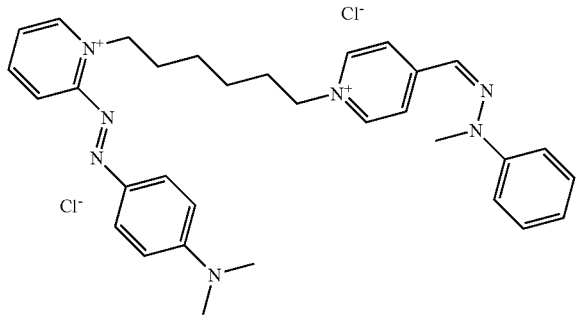

(**) Common dye support No. 1:

| | |
|---|---|
| Oleyl alcohol polyglycerolated with 2 mol of glycerol | 4 g |
| Oleyl alcohol polyglycerolated with 4 mol of glycerol (78% AM) | 5.69 g AM |
| Oleic acid | 3 g |
| Oleylamine 2 EO sold under the name Ethomeen 012 by the company Akzo | 7 g |
| Diethylaminopropyl laurylaminosuccinamate, sodium salt, at 55% AM | 3 g AM |
| Oleyl alcohol | 5 g |
| Oleic acid diethanolamide | 12 g |
| Propylene glycol | 3.5 g |
| Ethyl alcohol | 7 g |
| Dipropylene glycol | 0.5 g |
| Propylene glycol monomethyl ether | 9 g |
| Sodium metabisulfite as an aqueous solution containing 35% AM | 0.455 g |
| Ammonium acetate | 0.8 g |
| Antioxidant, sequestering agent | qs |
| Aqueous ammonia containing 20% $NH_3$ | 10 g |

Mode of Application

At the time of use, compositions A, B, and C were mixed weight-for-weight with a 20-volumes hydrogen peroxide solution. A final pH of 9.8 was obtained.

The mixture obtained was applied to locks of natural grey hair containing 90% white hairs and locks of bleached grey hair containing 90% white hairs, in a proportion of 10 g of mixture per 1 g of hair. After a leave-in time of 30 minutes at room temperature, the locks were rinsed, washed with a standard shampoo, rinsed again, and then dried.

The color of the hair was measured using a Minolta CM2002® spectrocolorimeter (illuminant D65-10° CSI) in the CIELab system. In this system, L* represents the lightness, a* represents the hue, and b* represents the saturation.

ΔE*ab, which represents the variation in color between a lock of natural hair and a lock of hair after dyeing, is obtained using the following formula:

$$\Delta E = \sqrt{(L^* - L_o^*)^2 + (a^* - a_o^*)^2 + (b^* - b_o^*)^2}$$

in which L* is the lightness, a* is the hue, and b* is the saturation of the lock of natural hair after dyeing; and $L_o^*$ is the lightness, $a_o^*$ is the hue, and $b_o^*$ is the saturation of the lock of hair after dyeing. The lower the value of ΔE, the less selective the dyeing of the hair.

The results obtained are presented in the table below.

| Composition | ΔE |
|---|---|
| A | 9.54 |
| B | 19.21 |
| C | 22.59 |

The above results show that the composition in accordance with the present disclosure leads to markedly less selective dyeing than the compositions of the prior art.

Example 2

Composition D was prepared by combining the following components:

| | |
|---|---|
| Oleyl alcohol polyglycerolated with 2 mol of glycerol | 4 g |
| Oleyl alcohol polyglycerolated with 4 mol of glycerol (78% AM) | 5.69 g AM |
| Oleic acid | 3 g |
| Oleylamine 2 EO sold under the name Ethomeen 012 by the company Akzo | 7 g |
| Diethylaminopropyl laurylaminosuccinamate, sodium salt, at 55% AM | 3 g AM |
| Oleyl alcohol | 5 g |
| Oleic acid diethanolamide | 12 g |
| Propylene glycol | 3.5 g |
| Ethyl alcohol | 7 g |
| Dipropylene glycol | 0.5 g |
| Propylene glycol monomethyl ether | 9 g |
| Sodium metabisulfite as an aqueous solution containing 35% AM | 0.455 g |
| Ammonium acetate | 0.8 g |
| 2,3-Diamino-6,7-dihydro-1H,5H-pyrazolo[1,2-a]pyrazol-1-one, 2 HCl | 1.36 g |
| 2-Methyl-5-hydroxyethylaminophenol | 1.00 g |
| Basic Yellow 28[†] | 0.5 g |
| Antioxidant, sequestering agent | qs |

-continued

| Aqueous ammonia containing 20% NH$_3$ | 10 g |
| Demineralized water | qs 100 g |

†Basic Yellow 28:

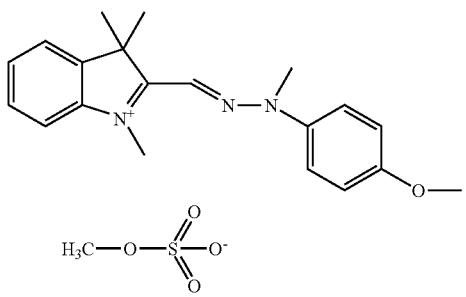

Mode of Application

At the time of use, composition D was mixed weight-for-weight with a 20-volumes hydrogen peroxide solution. A final pH of 9.8 was obtained.

The mixture obtained was applied to locks of natural grey hair containing 90% white hairs and locks of bleached grey hair containing 90% white hairs, in a proportion of 10 g of mixture per 1 g of hair. After a leave-in time of 30 minutes at room temperature, the locks were rinsed, washed with a standard shampoo, rinsed again, and then dried.

A strong golden-coppery tint was obtained, on both natural and bleached hair.

What is claimed is:

1. A composition for dyeing keratin fibers, comprising, in a suitable medium:
   (a) at least one oxidation base chosen from diamino-N,N-dihydropyrazolone derivatives of formula (I) and addition salts thereof:

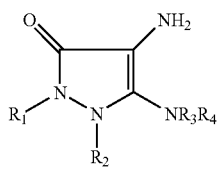

wherein:
   $R_1$, $R_2$, $R_3$, and $R_4$, which may be identical or different, are chosen from:
      linear and branched $C_1$-$C_{10}$ alkyl radicals optionally substituted with at least one radical chosen from $OR_5$ radicals, $NR_6R_7$ radicals, carboxyl radicals, sulfonic radicals, carboxamido radicals $CONR_6R_7$, sulfonamido radicals $SO_2NR_6R_7$, and heteroaryl and aryl radicals optionally substituted with at least one radical chosen from ($C_1$-$C_4$)alkyl, hydroxyl, $C_1$-$C_2$ alkoxy, amino, and (di)($C_1$-$C_2$)alkylamino groups;
      aryl radicals optionally substituted with at least one radical chosen from ($C_1$-$C_4$)alkyl, hydroxyl, $C_1$-$C_2$ alkoxy, amino, and (di)($C_1$-$C_2$)alkylamino radicals; and 5- or 6-membered heteroaryl radicals, optionally substituted with at least one radical chosen from ($C_1$-$C_4$)alkyl and ($C_1$-$C_2$)alkoxy radicals;
   $R_3$ and $R_4$ may also be hydrogen;
   $R_5$, $R_6$, and $R_7$, which may be identical or different, are chosen from:
      hydrogen;
      linear and branched $C_1$-$C_4$ alkyl radicals optionally substituted with at least one radical chosen from hydroxyl, $C_1$-$C_2$ alkoxy, carboxamido $CONR_8R_9$, sulfonyl $SO_2R_8$, and aryl radicals optionally substituted with at least one radical chosen from ($C_1$-$C_4$)alkyl, hydroxyl, $C_1$-$C_2$ alkoxy, amino, and (di)($C_1$-$C_2$)alkylamino radicals; and
      aryl radicals optionally substituted with at least one radical chosen from ($C_1$-$C_4$)alkyl, hydroxyl, $C_1$-$C_2$ alkoxy, amino, and (di)($C_1$-$C_2$)alkylamino radicals;
   $R_6$ and $R_7$, which may be identical or different, may also be chosen from carboxamido radicals $CONR_8R_9$ and sulfonyl radicals $SO_2R_8$;
   $R_8$ and $R_9$, which may be identical or different, are chosen from hydrogen; linear and branched $C_1$-$C_4$ alkyl radicals optionally substituted with at least one radical chosen from hydroxyl and $C_1$-$C_2$ alkoxy radicals;
   $R_1$ and $R_2$, and $R_3$ and $R_4$, may form, together with the nitrogen atoms to which they are attached, a saturated or unsaturated 5- to 7-membered heterocycle optionally substituted with at least one radical chosen from halogen atoms, amino radicals, (di)($C_1$-$C_4$)alkylamino radicals, hydroxyl radicals, carboxyl radicals, carboxamido radicals, ($C_1$-$C_2$)alkoxy radicals, and $C_1$-$C_4$ alkyl radicals optionally substituted with at least one radical chosen from hydroxyl, amino, (di) alkylamino, alkoxy, carboxyl, and sulfonyl radicals;
   $R_3$ and $R_4$ may also form, together with the nitrogen atom to which they are attached, a 5- or 7-membered heterocycle, the carbon atoms of which may be replaced with at least one entity chosen from optionally substituted oxygen and nitrogen atoms;
(b) at least one coupler; and
(c) at least one heterocyclic direct dye.

2. The composition of claim 1, wherein $R_1$ and $R_2$ are chosen from a $C_1$-$C_6$ alkyl radicals optionally substituted with at least one radical chosen from hydroxyl, ($C_1$-$C_2$) alkoxy, amino, (di)($C_1$-$C_2$)alkylamino, phenyl, methoxyphenyl, ethoxyphenyl, and benzyl radicals.

3. The composition of claim 2, wherein $R_1$ and $R_2$ are chosen from methyl, ethyl, 2-hydroxyethyl, 3-hydroxypropyl, 2-hydroxypropyl, and phenyl radicals.

4. The composition of claim 1, wherein $R_1$ and $R_2$ form, together with the nitrogen atoms to which they are attached, a saturated or unsaturated, optionally substituted 5- or 6-membered ring.

5. The composition of claim 1, wherein $R_1$ and $R_2$ form, together with the nitrogen atoms to which they are attached, a ring chosen from pyrazolidine and pyridazolidine rings, optionally substituted with at least one radical chosen from $C_1$-$C_4$ alkyl, hydroxyl, ($C_1$-$C_2$)alkoxy, carboxyl, carboxamido, amino, and (di)($C_1$-$C_2$)alkylamino radicals.

6. The composition of claim 1, wherein $R_1$ and $R_2$ form, together with the nitrogen atoms to which they are attached, a ring chosen from pyrazolidine and pyridazolidine rings.

7. The composition of claim 1, wherein $R_3$ and $R_4$ are chosen from hydrogen and linear and branched $C_1$-$C_6$ alkyl radicals optionally substituted with at least one radical chosen from hydroxyl, $(C_1-C_2)$alkoxy, amino, and $(di)(C_1-C_2)$alkylamino radicals; and phenyl radicals optionally substituted with at least one radical chosen from hydroxyl, amino, and $(C_1-C_2)$alkoxy radicals.

8. The composition of claim 1, wherein $R_3$ and $R_4$ are chosen from hydrogen, methyl radicals, ethyl radicals, isopropyl radicals, 2-hydroxyethyl radicals, 3-hydroxypropyl radicals, 2-hydroxypropyl radicals, and 2-carboxyethyl radicals.

9. The composition of claim 8, wherein $R_3$ and $R_4$ are hydrogen.

10. The composition of claim 1, wherein $R_3$ and $R_4$ form, together with the nitrogen atom to which they are attached, a 5- or 7-membered ring chosen from pyrrolidine, piperidine, homopiperidine, piperazine, and homopiperazine heterocycles; said rings possibly being substituted with at least one radical chosen from hydroxyl, amino, $(di)(C_1-C_2)$alkylamino, carboxyl, carboxamido, and $C_1-C_4$ alkyl radicals optionally substituted with at least one radical chosen from hydroxyl, amino, and $C_1-C_2$ (di)alkylamino radicals.

11. The composition of claim 1, wherein $R_3$ and $R_4$ form, together with the nitrogen atom to which they are attached, a 5- or 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine, and N-(2-hydroxyethyl)homopiperazine.

12. The composition of claim 1, wherein $R_3$ and $R_4$ form, together with the nitrogen atom to which they are attached, a 5- or 7-membered ring chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, hydroxypiperidine, homopiperidine, diazepane, N-methylhomopiperazine, and N-β-hydroxyethylhomopiperazine.

13. The composition of claim 1, wherein $R_3$ and $R_4$ form, together with the nitrogen atom to which they are attached, a 5-membered ring chosen from pyrrolidine, 3-hydroxypyrrolidine, 3-aminopyrrolidine, and 3-dimethylaminopyrrolidine.

14. The composition of claim 1, wherein the at least one oxidation base chosen from compounds of formula (I) and addition salts thereof, is chosen from:
2,3-diamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
4,5-diamino-1,2-dimethyl-1,2-dihydropyrazol-3-one;
4,5-diamino-1,2-diethyl-1,2-dihydropyrazol-3-one;
4,5-diamino-1,2-di-(2-hydroxyethyl)-1,2-dihydropyrazol-3-one;
2-amino-3-(2-hydroxyethyl)amino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
4-amino-1,2-diethyl-5-pyrrolidin-1-yl-1,2-dihydropyrazol-3-one;
4-amino-5-(3-dimethylaminopyrrolidin-1-yl)-1,2-diethyl-1,2-dihydropyrazol-3-one; and
2,3-diamino-6-hydroxy-6,7-dihydro-1H,5H-pyrazolo[1,2-a]pyrazol-1-one.

15. The composition of claim 1, wherein the at least one coupler is chosen from meta-phenylenediamines, meta-aminophenols, meta-diphenols, naphthalene-based couplers, heterocyclic couplers, and the addition salts thereof.

16. The composition of claim 15, wherein the at least one coupler is chosen from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the acid addition salts thereof.

17. The composition of claim 1, wherein the at least one coupler is present in the composition in an amount ranging from 0.001% to 10% by weight relative to the total weight of the dye composition.

18. The composition of claim 1, wherein the at least one heterocyclic direct dye comprises in its structure at least one heterocycle chosen from thiophene, thianthrene, furan, 1,4-pyran, 1,2-pyran, isobenzofuran, chromene, xanthene, 2H-pyrrole, pyrrole, imidazole, pyrazole, isothiazole, isoxazole, pyridine, pyrazine, pyrimidine, pyridazine, indolizine, isoindole, 3H-indole, indole, 1H-indazole, purine, 4H-quinolizine, isoquinoline, quinoline, phthalazine, naphthyridine, quinoxaline, cinnoline, pteridine, carbazole, 4a,H-carbazole, carboline, phenanthridine, acridine, perimidine, phenanthroline, phenazine, phenothiazine, furazan, phenoxazine, phenoxathine, pyrrolidine, isochroman, chroman, pyrroline, imidazoline, imidazolidine, pyrazoline, pyrazolidine, morpholine, benzisoquinoline, imidazothiazole, benzothiazole, benzofuran, 1,2,3-triazole, 1,2,4-triazole, isoazole, 1,4-oxazine, o- or p-isoxazine, 1,2,5-oxathiazine, 1,2,6-oxathiazine, 1,4,2-oxadiazine, 1,3,5,2-oxadiazine, 3-isopyrrole, indene, isoindene, indoline, isoindoline, 1,2,3,4-oxatriazole, 1,2,3,5-oxatriazole, piperazine, piperidine, 1,3,5-triazine, 1,2,4-triazine, 1,2,3-triazine, 1,3,2-benzoxazine, 1,4,2-benzoxazine, isocoumarin, 1,2,3-dioxazole, 1,2,4-dioxazole, 1,3,2-dioxazole, 1,3,4-dioxazole, 1,2,5-oxathiazole, 1,3-oxathiol, 1,2,3,4-tetrahydroquinoxaline, quinazoline, pyrazolotriazole, thiazole, and indolenine rings, optionally substituted with at least one substituent, and homologues thereof including at least one carbonyl group.

19. The composition of claim 18, wherein the at least one substituent is chosen from optionally substituted linear or branched $C_1$-$C_{10}$ alkyl, amino, hydroxyl, halogen, linear or branched $C_2$-$C_{10}$ alkenyl, $C_1$-$C_{10}$ mono- or polyhydroxyalkyl, $C_1$-$C_{10}$ mono- or polyaminoalkyl, mono- or di($C_1$-$C_6$)alkylamino, mono- or dihydroxy($C_1$-$C_6$)alkylamino, mono ($C_1$-$C_6$)alkylmonohydroxy($C_1$-$C_6$)alkylamino, mono- or di($C_1$-$C_6$)alkylamino($C_1$-$C_{10}$)alkyl, mono- or dihydroxy($C_1$-$C_6$)alkylamino($C_1$-$C_{10}$)alkyl, mono($C_1$-$C_6$)-alkylmonohydroxy($C_1$-$C_6$)alkylamino($C_1$-$C_{10}$)alkyl, nitro, carboxyl, carboxy($C_1$-$C_{10}$)alkyl, ($C_1$-$C_6$)alkoxycarbonyl, sulfo, sulfo($C_1$-$C_{10}$)alkyl, ($C_1$-$C_{10}$)alkoxy, ureido, tri($C_1$-$C_6$)alkylammonium, tri($C_1$-$C_6$)alkylammonium($C_1$-$C_{10}$)alkyl, and ($C_8$-$C_{30}$)aryl radicals.

20. The composition of claim 1, wherein the at least one heterocyclic direct dye is neutral.

21. The composition of claim 20, wherein the at least one neutral heterocyclic direct dye is chosen from those comprising at least one ring chosen from pyridine, quinoxaline, pyrazoline, pyrazole, oxadiazole, thiazole, pyrrole, indole, pyrazolotriazole, quinoline, indoline, phenazine, coumarin, and benzopyran rings, and homologues thereof including at least one carbonyl group.

22. The composition of claim 21, wherein the at least one neutral heterocyclic direct dye is chosen from 2,5-diamino-6-nitropyridine, 5-amino-2-(2'-hydroxyethyl)amino-6-nitropyridine, 2-amino-5-(2'-hydroxyethyl)amino-6-nitropyridine, 5-amino-2-ethylamino-6-nitropyridine, 2-ethylamino-5-(2'-hydroxyethyl)amino-6-nitropyridine, 2-methylamino-5-(2'-hydroxyethyl)amino-6-nitropyridine, 1,2,3,4-tetrahydro-6-nitroquinoxaline, 2,3-indolinedione, Vat Blue 6, Disperse Yellow 184, brasiline, and hematoxylin.

23. The composition of claim 1, wherein the at least one heterocyclic direct dye is anionic.

24. The composition of claim 23, wherein the at least one anionic heterocyclic direct dye is chosen from those comprising at least one ring chosen from pyrazole, xanthene, quinoline, benzotriazole, benzoquinoline, indoline, and naphthotriazole rings, and homologues thereof including at least one carbonyl group.

25. The composition of claim 24, wherein the at least one anionic heterocyclic direct dye is chosen from Acid Yellow 23, Acid Yellow 73, Acid Red 92, Acid Yellow 3, Food Yellow 4, Acid Red 51, Acid Red 52, Acid Red 87, Acid Red 95, Acid Red 92, Acid Blue 74, Acid Red 195, Acid Orange 92, Acid Yellow 5, Acid Black 70, Direct Yellow 106, Direct Yellow 59, and Acid Yellow 14.

26. The composition of claim 1, wherein the at least one heterocyclic direct dye is cationic.

27. The composition of claim 26, wherein the at least one cationic heterocyclic direct dye has at least one cationic charge belonging to a heterocycle.

28. The composition of claim 26, wherein the at least one heterocyclic direct dye is chosen from cationic dyes comprising at least one xanthene ring, cationic dyes comprising at least one acridene ring, cationic dyes comprising at least one benzothiazole ring, cationic dyes comprising at least one phenothiazine ring, cationic dyes comprising at least one pyrazole ring, cationic dyes comprising at least one triazole rings, cationic dyes comprising at least one thiazole ring, cationic dyes comprising at least one phenazine ring, cationic dyes comprising at least one indolenine ring, cationic dyes comprising at least one phenoxazine ring, cationic dyes comprising at least one imidazole ring, cationic dyes comprising at least one pyridine ring, and homologues thereof including at least one carbonyl group.

29. The composition of claim 28, wherein the at least one cationic heterocyclic direct dye is chosen from Basic Red 1, Basic Red 3, Basic Red 4, Basic Violet 10 and Basic Violet 11, Basic Orange 15, Basic Orange 16, Basic Orange 17, Basic Blue 41, Basic Blue 67, Basic Blue 9, Basic Yellow 57, Basic Red 22, Basic Red 46, Basic Red 29, Basic Red 2, Basic Red 14, Basic Yellow 13, Basic Yellow 28, Basic Yellow 29, Basic Blue 6, Basic Red 51, Basic Orange 31, and Basic Yellow 87.

30. The composition of claim 1, wherein the at least one heterocyclic direct dye is present in the dye composition in an amount, for each heterocyclic direct dye, ranging from 0.0001% to 30% by weight relative to the total weight of the dye composition.

31. The composition of claim 1, further comprising at least one additional oxidation base chosen from para-phenylenediamines, bis(phenyl)alkylenediamines, para-aminophenols, bis-para-aminophenols, ortho-aminophenols, ortho-phenylenediamines, heterocyclic bases other than the compounds of formula (I), and the addition salts thereof.

32. The composition of claim 1, wherein the at least one additional oxidation base is present in the dye composition in an amount ranging from 0.001% to 10% by weight relative to the total weight of the dye composition.

33. The composition of claim 1, further comprising at least one oxidizing agent.

34. A method for dyeing keratin fibers, comprising applying a dye composition to the keratin fibers in the presence of an oxidizing agent for a time that is sufficient to develop a desired coloration, wherein the dye composition comprises, in a suitable medium:
(a) at least one oxidation base chosen from diamino-N,N-dihydropyrazolone derivatives of formula (I) and addition salt thereofs:

(I)

$$\begin{array}{c}\text{structure}\end{array}$$

wherein:
$R_1$, $R_2$, $R_3$, and $R_4$, which may be identical or different, are chosen from:
linear and branched $C_1$-$C_{10}$ alkyl radicals optionally substituted with at least one radical chosen from $OR_5$ radicals, $NR_6R_7$ radicals, carboxyl radicals, sulfonic radicals, carboxamido radicals $CONR_6R_7$, sulfonamido radicals $SO_2NR_6R_7$, and heteroaryl and aryl radicals optionally substituted with at least one radical chosen from ($C_1$-$C_4$)alkyl, hydroxyl, $C_1$-$C_2$ alkoxy, amino, and (di)($C_1$-$C_2$)alkylamino groups;
aryl radicals optionally substituted with at least one radical chosen from ($C_1$-$C_4$)alkyl, hydroxyl, $C_1$-$C_2$ alkoxy, amino, and (di)($C_1$-$C_2$)alkylamino radicals;
5- or 6-membered heteroaryl radicals, optionally substituted with at least one radical chosen from ($C_1$-$C_4$)alkyl and ($C_1$-$C_2$)alkoxy radicals;
$R_3$ and $R_4$ may also be hydrogen;
$R_5$, $R_6$, and $R_7$, which may be identical or different, are chosen from:
hydrogen;
linear and branched $C_1$-$C_4$ alkyl radicals optionally substituted with at least one radical chosen from hydroxyl, $C_1$-$C_2$ alkoxy, carboxamido $CONR_8R_9$, sulfonyl $SO_2R_8$, and aryl radicals optionally substituted with at least one radical chosen from $(C_1-C_4)$alkyl, hydroxyl, $C_1-C_2$ alkoxy, amino, and (di)$(C_1-C_2)$alkylamino radicals; and aryl radicals optionally substituted with at least one radical chosen from $(C_1-C_4)$alkyl, hydroxyl, $C_1-C_2$ alkoxy, amino, and (di)$(C_1-C_2)$alkylamino radicals;

$R_6$ and $R_7$, which may be identical or different, may also be chosen from carboxamido radicals $CONR_8R_9$ and sulfonyl radicals $SO_2R_8$;

$R_8$ and $R_9$, which may be identical or different, are chosen from hydrogen; linear and branched $C_1-C_4$ alkyl radicals optionally substituted with at least one radical chosen from hydroxyl and $C_1-C_2$ alkoxy radicals;

$R_1$ and $R_2$, and $R_3$ and $R_4$, may form, together with the nitrogen atoms to which they are attached, a saturated or unsaturated 5- to 7-membered heterocycle optionally substituted with at least one radical chosen from halogen atoms, amino radicals, (di)$(C_1-C_4)$alkylamino radicals, hydroxyl radicals, carboxyl radicals, carboxamido radicals, $(C_1-C_2)$alkoxy radicals, and $C_1-C_4$ alkyl radicals optionally substituted with at least one radical chosen from hydroxyl, amino, (di) alkylamino, alkoxy, carboxyl, and sulfonyl radicals;

$R_3$ and $R_4$ may also form, together with the nitrogen atom to which they are attached, a 5- or 7-membered heterocycle, the carbon atoms of which may be replaced with at least one entity chosen from optionally substituted oxygen and nitrogen atoms;

(b) at least one coupler; and
(c) at least one heterocyclic direct dye.

35. The method of claim 34, wherein the at least one oxidizing agent is chosen from hydrogen peroxide, urea peroxide, alkali metal bromates, persalts, peracids, and oxidase enzymes.

36. A multi-compartment device, wherein at least one first compartment contains a dye composition and at least one second compartment contains at least one oxidizing agent, wherein the dye composition comprises, in a suitable medium:

(a) at least one oxidation base chosen from diamino-N,N-dihydropyrazolone derivatives of formula (I) and addition salt thereofs:

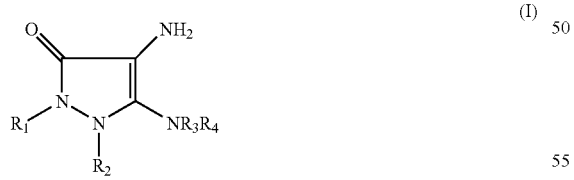

(I)

wherein:
$R_1$, $R_2$, $R_3$, and $R_4$, which may be identical or different, are chosen from:

linear and branched $C_1-C_{10}$ alkyl radicals optionally substituted with at least one radical chosen from $OR_5$ radicals, $NR_6R_7$ radicals, carboxyl radicals, sulfonic radicals, carboxamido radicals $CONR_6R_7$, sulfonamido radicals $SO_2NR_6R_7$, and heteroaryl and aryl radicals optionally substituted with at least one radical chosen from $(C_1-C_4)$alkyl, hydroxyl, $C_1-C_2$ alkoxy, amino, and (di)$(C_1-C_2)$alkylamino groups;

aryl radicals optionally substituted with at least one radical chosen from $(C_1-C_4)$alkyl, hydroxyl, $C_1-C_2$ alkoxy, amino, and (di)$(C_1-C_2)$alkylamino radicals;

5- or 6-membered heteroaryl radicals, optionally substituted with at least one radical chosen from $(C_1-C_4)$alkyl and $(C_1-C_2)$alkoxy radicals;

$R_3$ and $R_4$ may also be hydrogen;

$R_5$, $R_6$, and $R_7$, which may be identical or different, are chosen from:
hydrogen;
linear and branched $C_1-C_4$ alkyl radicals optionally substituted with at least one radical chosen from hydroxyl, $C_1-C_2$ alkoxy, carboxamido $CONR_8R_9$, sulfonyl $SO_2R_8$, and aryl radicals optionally substituted with at least one radical chosen from $(C_1-C_4)$alkyl, hydroxyl, $C_1-C_2$ alkoxy, amino, and (di)$(C_1-C_2)$alkylamino radicals; and aryl radicals optionally substituted with at least one radical chosen from $(C_1-C_4)$alkyl, hydroxyl, $C_1-C_2$ alkoxy, amino, and (di)$(C_1-C_2)$alkylamino radicals;

$R_6$ and $R_7$, which may be identical or different, may also be chosen from carboxamido radicals $CONR_8R_9$ and sulfonyl radicals $SO_2R_8$;

$R_8$ and $R_9$, which may be identical or different, are chosen from hydrogen; linear and branched $C_1-C_4$ alkyl radicals optionally substituted with at least one radical chosen from hydroxyl and $C_1-C_2$ alkoxy radicals;

$R_1$ and $R_2$, and $R_3$ and $R_4$, may form, together with the nitrogen atoms to which they are attached, a saturated or unsaturated 5- to 7-membered heterocycle optionally substituted with at least one radical chosen from halogen atoms, amino radicals, (di)$(C_1-C_4)$alkylamino radicals, hydroxyl radicals, carboxyl radicals, carboxamido radicals, $(C_1-C_2)$alkoxy radicals, and $C_1-C_4$ alkyl radicals optionally substituted with at least one radical chosen from hydroxyl, amino, (di) alkylamino, alkoxy, carboxyl, and sulfonyl radicals;

$R_3$ and $R_4$ may also form, together with the nitrogen atom to which they are attached, a 5- or 7-membered heterocycle, the carbon atoms of which may be replaced with at least one entity chosen from optionally substituted oxygen and nitrogen atoms;

(b) at least one coupler; and
(c) at least one heterocyclic direct dye.

* * * * *